United States Patent
Yousaf

(10) Patent No.: US 9,968,683 B2
(45) Date of Patent: May 15, 2018

(54) METHOD FOR CONJUGATING MOLECULES

(71) Applicant: Muhammad Naveed Yousaf, Mississauga (CA)

(72) Inventor: Muhammad Naveed Yousaf, Mississauga (CA)

(73) Assignee: ORGANOLINX CORP., Mississauga (CA)

( * ) Notice: Subject to any disclaimer, the term of this patent is extended or adjusted under 35 U.S.C. 154(b) by 0 days. days.

(21) Appl. No.: 14/972,782

(22) Filed: Dec. 17, 2015

(65) Prior Publication Data

US 2016/0206748 A1    Jul. 21, 2016

Related U.S. Application Data

(60) Provisional application No. 62/092,889, filed on Dec. 17, 2014.

(51) Int. Cl.

| | | |
|---|---|---|
| *C07D 211/90* | (2006.01) | |
| *C07D 213/82* | (2006.01) | |
| *C07D 211/82* | (2006.01) | |
| *A61K 47/48* | (2006.01) | |
| *A61K 47/54* | (2017.01) | |
| *A61K 47/55* | (2017.01) | |

(52) U.S. Cl.
CPC ........ *A61K 47/48023* (2013.01); *A61K 47/54* (2017.08); *A61K 47/551* (2017.08)

(58) Field of Classification Search
None
See application file for complete search history.

(56) References Cited

U.S. PATENT DOCUMENTS

| | | | |
|---|---|---|---|
| 4,861,597 A | 8/1989 | Kida et al. | |
| 6,417,326 B1 | 7/2002 | Cullis et al. | |
| 9,080,144 B2 | 7/2015 | Yousaf | |
| 2007/0249060 A1 | 10/2007 | Kirschner et al. | |
| 2010/0063135 A1 | 3/2010 | Dande et al. | |
| 2012/0100077 A1 | 4/2012 | Hoffmann et al. | |
| 2013/0302891 A1 | 11/2013 | Yousaf | |

FOREIGN PATENT DOCUMENTS

| | | |
|---|---|---|
| CN | 102051239 A1 | 5/2011 |
| WO | 2013/173392 A1 | 11/2013 |
| WO | 2014/197991 A1 | 12/2014 |

OTHER PUBLICATIONS

Foos, J. et al. Synthesis and Nuclear Magnetic Resonance Spectra of N-Carboethoxy-4-spiro-1,4-dihydropyridines. J. Org. Chem. 1979, vol. 44, p. 2524.*
STN International Search—dated Dec. 10, 2014.
International Search Report and Written Opinion of PCT/CA2014/050547 dated Sep. 29, 2014.
Dutta et al., Synthetic Chemoselective Rewiring of Cell Surfaces: Generation of Three-Dimensional Tissue Structures, J. Am. Chem. Soc., 2011, 133 (22), 8704-8713.
Dutta et al., "Engineering Cell Surfaces via Liposome Fusion", Bioconjugate Chem., 2011, 22 (12), 2423-2433.
Selden, Nicholas et al., "Chemically Programmed Cell Adhesion with Membrane-Anchored Oligonucleotides", J. Am. Chem. Soc., 2012, 134(2), 765-768.
Wilson, J.T. et al., "Noncovalent Cell Surface Engineering with Cationic Graft Copolymers", J. Am. Chem. Soc., 2009, 131 (51), 18228-18229.
Gong, Yun et al., "Membrane Activation: Selective Vesicle Fusion via Small Molecule Recognition", J. Am. Chem. Soc., 2006, 128 (45), 14430-14431.
Holland, JW et al., "Poly(ethylene glycol)—Lipid Conjugates Regulate the Calcium-Induced Fusion of Liposomes Composed of Phosphatidylethanolamine and Phosphatidylserine", Biochemistry., 1996, 35(8), 2618-2624.
Faiss, Simon et al., "Adhesion and rupture of liposomes mediated by electrostatic interaction monitored by thickness shear mode resonators" Eur Biophys J (2004) 33, 551-561.

\* cited by examiner

*Primary Examiner* — Niloofar Rahmani
(74) *Attorney, Agent, or Firm* — Bereskin & Parr LLP/S.E.N.C.R.L., S.R.L.

(57) ABSTRACT

Methods of conjugating two molecules are disclosed herein in which a non-polymeric aliphatic dialdehyde or non-polymeric aromatic dialdehyde is reacted with a compound comprising an amine ($NH_2$) moiety to form a stable product under mild conditions.

18 Claims, 5 Drawing Sheets

Rhodamine;

Fluorescein;

Biotin;

NBD;

Carbohydrate;

BODIPY™;

BODIPY™ FL;

Crosslinker;

Lipid;

Ferrocene;

Cy3;

Cy 5;

Cy 5.5;

Small-molecules:

METHOD FOR CONJUGATING MOLECULES

FIELD

The present application relates to compounds and methods for the conjugation of molecules.

BACKGROUND

Of the known methods for the conjugation of molecules, the Huigsen [3+2] "click" chemistry and activated carboxylic acid conjugation reactions are perhaps two of most common. Scheme 1 shows the standard Huigsen [3+2] conjugation which uses Cu(I) as a catalyst. One of the drawbacks of this method is the need to use a metal catalyst.

Scheme 1

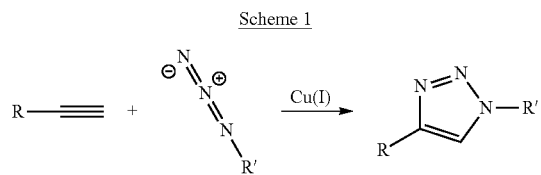

Scheme 2 shows the classic activated carboxylic acid-amine conjugation using N-hydroxysuccinamide as the activating group.

Scheme 2

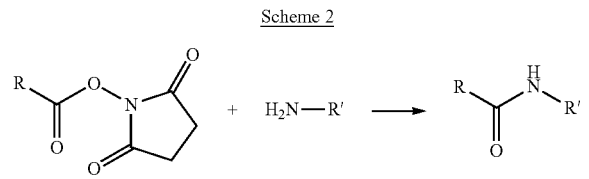

The N-hydroxysuccinamide activated ester is one of the best-selling bio-conjugation reagents. One of the drawbacks of this reagent is the necessity to remove the N-hydroxysuccinamide side product formed in the reaction.

Nagasaki et al.[1] describe the reaction between a bioactive compound having at least one amino group with a functionalized polyethylene glycol having a structure that allows reaction of two aldehyde groups with one amino group to form two covalent bonds.

Miao et al.[2] describe a conjugation reaction between an amine and a dialdehyde in the presence of a reducing agent (NaBH$_3$(CN)) at a pH of 3-9 to provide a fully saturated cyclic structure.

SUMMARY

It has been found in the present studies that a non-polymeric, small molecule aliphatic or aromatic dialdehyde can be used to conjugate with a variety of molecules comprising an amine moiety. The compounds and methods disclosed herein provide an alternate method to conjugate molecules with amine-containing compounds that employs stable starting materials, produces stable products and is versatile, fast, efficient and straightforward to perform. In the methods of the present application a non-polymeric compound comprising a dialdehyde moiety is reacted with a compound comprising an amine moiety. The method requires no catalysts, no reducing agents, can be performed under aqueous and/or physiological conditions, is irreversible and produces no side products that must be removed to isolate the desired product.

The present application therefore includes a method for conjugating two molecules together comprising reacting a non-polymeric aliphatic dialdehyde or non-polymeric aromatic dialdehyde with a compound comprising an NH$_2$ moiety under conditions for the conjugation of the NH$_2$ moiety with the dialdehyde to form a conjugated product. The method is performed in the absence of a reducing agent.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The embodiments of the application will now be described in greater detail with reference to the attached drawings in which.

DETAILED DESCRIPTION

I. Definitions

Figure 1:
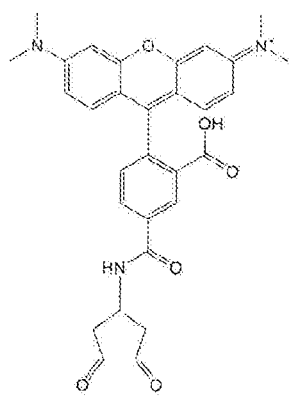
FIG. 1 shows representative compounds of Formula I, wherein R$^1$ is a lipid, metal complex, fluorophore, ligand, carbohydrate and C$_{1-10}$alkyl.
Figure 1:
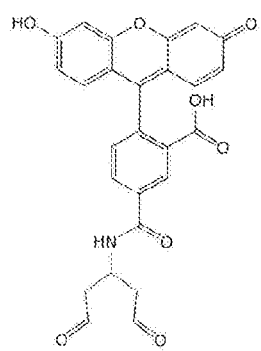
Figure 1:
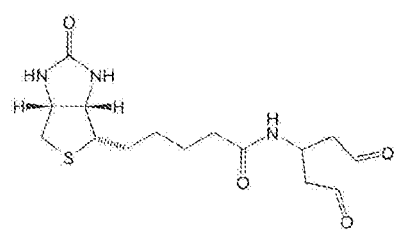
Figure 1:
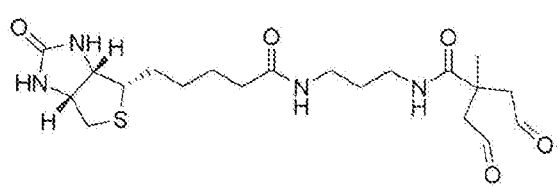
Figure 1:
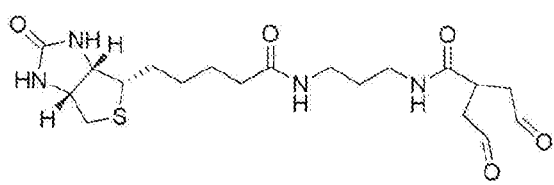
Figure 1:
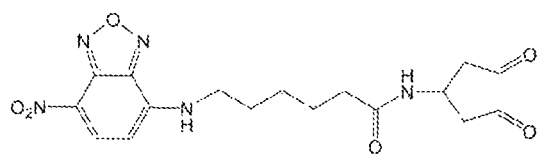
Figure 1:
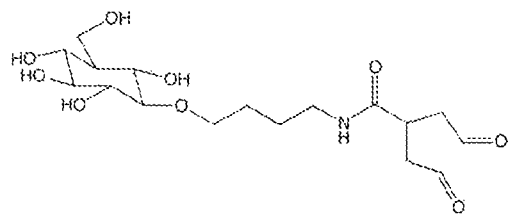
Figure 1:
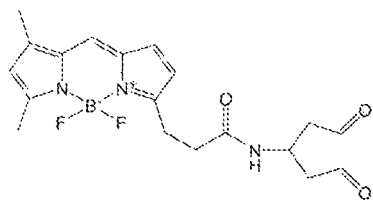
Figure 1:
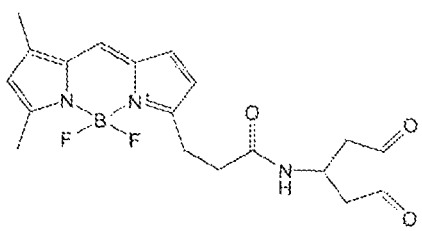
Figure 1:
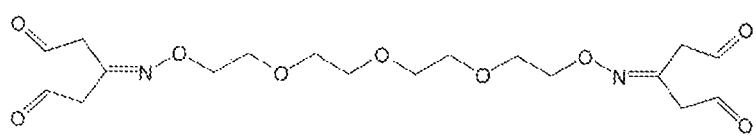
Figure 1:
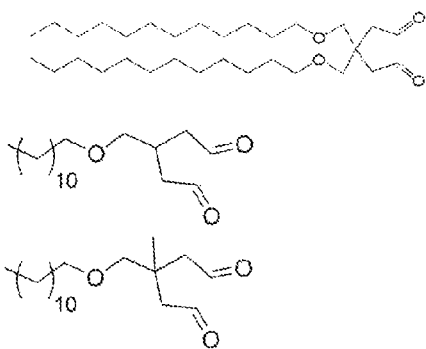
Figure 1:
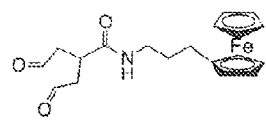
Figure 1:
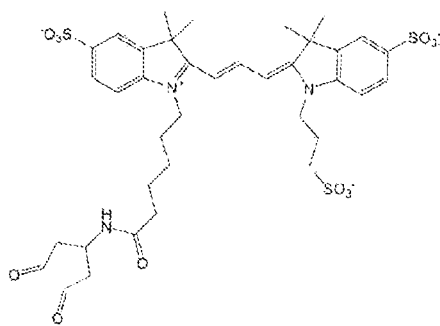
Figure 1:
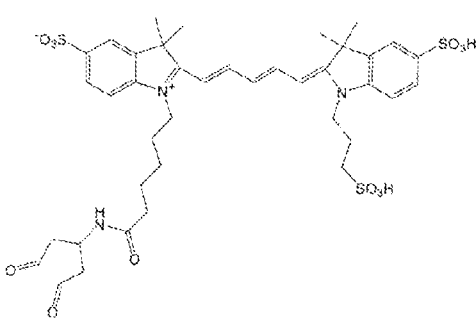
Figure 1:
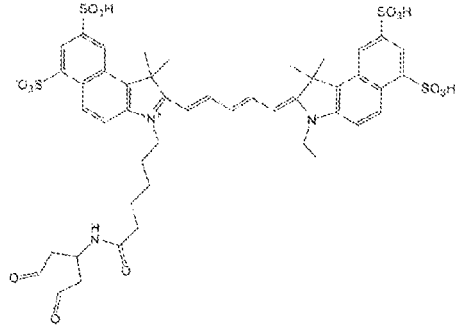
Figure 1:
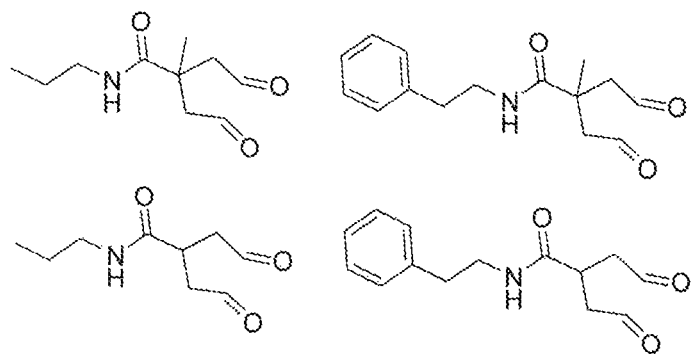

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The present description refers to a number of chemical terms and abbreviations used by those skilled in the art. Nevertheless, definitions of selected terms are provided for clarity and consistency.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-6}$alkyl means an alkyl group having 1, 2, 3, 4, 5 or 6 carbon atoms. It is an embodiment of the application that, in the alkyl groups, one or more, including all, of the available hydrogen atoms are optionally replaced with F or $^2$H and thus include, for example trifluoromethyl, pentafluoroethyl and the like.

The term "aryl" as used herein, whether it is used alone or as part of another group, refers to mono-, bi- or tricyclic groups that contain at least one aromatic carbocycle. In an embodiment of the present application, the aryl group contains 6, 9, 10 or 14 carbon atoms, such as phenyl, naphthyl, indanyl or anthracenyl. It is an embodiment of the application that, in the aryl groups, one or more, including all, of the available hydrogen atoms are optionally replaced with F or $^2$H and thus include, for example pentafluorophenyl and the like.

Hex as used herein refers to the organic solvent, hexanes.

DCM as used herein refers to the organic solvent, dichloromethane.

THF as used herein refers to the organic solvent, tetrahydrofuran.

EtOAc as used herein refers to the organic solvent, ethyl acetate.

ACN as used herein refers to the organic solvent, acetonitrile.

MeOH as used herein refers to the organic solvent, methanol.

MeOD as used herein refers to deuterated methanol.

TLC as used herein refers to thin layer chromatography.

HBTU as used herein refers to the peptide coupling agent, 2-(1H-benzotriazol-1-yl)-1, 1, 3, 3-tetramethyluronium hexafluorophosphate.

TEA as used herein refers to triethylamine.

TFA as used herein refers to trifluoroacetic acid.

The term "solid support" as used herein refers any solid support to which chemical molecules can be adhered. In an embodiment of the application, the solid support comprises a substantially planar surface. In another embodiment of the application, the solid support comprises a substantially bead-like shape. In further embodiments, the solid support is made from paper, glass, plastic, polymers, metals, ceramics, alloys or composites.

The term "labeling moiety" as used herein refers to any moiety that is used for detection of molecules. Different types of labels are known in the art depending on the form of detection to be used. For example, the labeling moiety is selected from a radiolabel, a fluorescent label, a spin label, isotope label, a positron emission tomography (PET) and a single-photon emission computed tomography label.

The term "binding moiety" as used herein refers to any moiety that binds to a receptor or active site in molecule. In an embodiment, the binding is specific binding, that is, the binding moiety will bind to one receptor or active site preferentially over other receptors or active sites.

The term "targeting moiety" as used herein means a moiety which is taken up and retained in particular site of a subject such as a biological structure for example an organ or tissue or a pathological structure for example a tumor, with little or no accumulation and/or retention in non-target sites over a particular time period. In an embodiment, the targeting moiety also is a moiety that is an inhibitor of a protein, for example a protein that is overexpressed in a disease, disorder or condition such as cancer. In another embodiment, the targeting vector is an antibody. Targeting moieties are known and the selection of a suitable targeting moiety for a particular imaging or therapeutic use can be made by a person skilled in the art. Targeting moieties include, but are not limited to small molecules such as enzyme inhibitors or pharmaceutical-like compounds, peptides, proteins, nucleic acids or analogues or derivatives thereof, dendrimers, polymers and antibodies or fragments thereof.

The term "fluorophore" as used herein refers to a chemical moiety that is fluorescent and that can re-emit light upon light excitation. Fluorophores are known and the selection of a suitable fluorophore can be made by a person skilled in the art. Examples of fluorophores include, but are not limited to fluorescein and derivatives thereof, cyanine dyes, metal-based fluorophores, boron-dipyrromethene (BODIPY) dyes, sulforhodamine 101 acid chloride (Texas Red), Alexa Fluor™ dyes and rhodamine dyes.

The term "immunogenic moiety" as used herein refers to a moiety which induces an immune response in a subject. For example, the immunogenic moiety is a moiety for which the subject has antibodies against. In an embodiment, the immunogenic moiety is a hapten such as a dinitrophenyl group.

The term "hapten" as used herein refers to a small molecule that can elicit an immune response only when attached to a large carrier such as a protein. The carrier may be one that also does not elicit an immune response by itself.

The term "nucleic acid" as used herein includes all forms of oligonucleotides, deoxyribonucleic acid (DNA) and ribonucleic acid (RNA). Nucleic acids are either isolated from natural sources or prepared using well-known synthetic techniques. All forms of DNA and RNA, both single and double stranded, are included in the present application, for example, genomic DNA, complementary DNA (cDNA), plasmid DNA (pDNA), messenger RNA (mRNA), transfer RNA (tRNA), transfer-messenger RNA (tmRNA), ribosomal RNA (rRNA), small interfering RNA (siRNA), microRNA (miRNA), piwi-interacting RNA (piRNA), antisense RNA (aRNA), RNA interference (RNAi), small nuclear RNA (snRNA) and small nucleolar RNA (snoRNA), and portions thereof. Nucleic acids also include artificial analogs of natural nucleic acids that have been designed and synthesized for example, to improve stability, and include, for example, peptide nucleic acids, morpholino nucleic acids, locked nucleic acids, glycose nucleic acids and threose nucleic acids. Each of these later nucleic acid analogs is distinguished from naturally occurring DNA or RNA by changes to the backbone of the molecule. In an embodiment, the nucleic acid is any sequence of nucleotides that is used for diagnostic, therapeutic and/or cell monitoring applications.

The term "amino acid" as used herein refers to an organic compound comprising amine (—$NH_2$) and carboxylic acid (—COOH) functional groups, along with a side-chain specific to each amino acid. The key elements of an amino acid are carbon, hydrogen, oxygen and nitrogen, though other elements are found in the side-chains of certain amino acids, including S and Se. About 500 amino acids are known in nature[3]. They can be classified, for example, according to the core structural functional groups' locations as alpha ($\alpha$), beta ($\beta$), gamma ($\gamma$) or delta ($\delta$), amino acids; other categories relate to polarity, pH level, and side-chain group type (e.g. acidic, basic, neutral, aliphatic, acyclic, aromatic, containing hydroxyl or sulfur, etc.). In an embodiment, the amino acid is one of the 23 proteinogenic amino acids, that is amino acids that are precursors to proteins, and are incorporated into proteins during translation. In an embodiment, the amino acid is a derivative or analog of a naturally occurring amino acid.

The term "derivative of a naturally occurring amino acid" as used herein refers to a naturally occurring amino acid, or an analog thereof, containing a modified functional group, such as a naturally occurring amino acid, or analog thereof, in which the amino group, the carboxyl group and/or a side chain function group has been derivatized. Examples of such groups include, but are not limited to, $C_{1-10}$alkyl-, aryl- and $C_{1-6}$alkylenearyl-functionalized amines, carboxylic acids, hydroxyls, thiols and/or amides, including di-functionalization of a group where possible (for example amines and amides). In a further embodiment, such groups include methyl-, ethyl, aryl- and benzyl-functionalized carboxylic acids, hydroxyls and/or thiols and/or methyl-, dimethyl-, ethyl-, diethyl, aryl-, diaryl, benzyl and dibenzyl-functionalized amines and/or amides. Amino acid derivatives are either naturally occurring or are synthetic.

The term "analog of a naturally occurring amino acid" as used herein refers to a naturally occurring amino acid, or a derivative thereof, in which one or more of the functional groups have been modified, for example oxidized, reduced, functionalized or removed, replaced with a functionally similar functional group, or moved to a different location on the amino acid molecule. Examples of such compounds are well known and studied in the art, and include, for example, $\beta$-amino acids, fluorinated amino acids and $\alpha$-hydroxy analogs. Amino acid analogs are either naturally occurring or are synthetic.

The term "linker moiety" as used herein refers to any molecular structure that joins two or more other molecular structures together. In an embodiment, the linker moiety comprises at least one ester or amide linkage although a person skilled in the art would appreciate that other linker moieties, such as ethers, thioethers, thioamides, thioesters and/or amines can additionally, or alternatively, be present. In a further embodiment, the linker group also comprises one or more $C_1$-$C_{20}$alkylene groups, such groups being either straight chain or branched chain alkylene groups.

The term "small molecule" as used herein refers to a molecule having a low molecular weight with a size on the order of $10^{-9}$ m. In an embodiment, the small molecule has a molecular weight less than about 900 daltons. In a further embodiment, the small molecule has a molecular weight less than about 500 daltons.

The term "non-polymeric" as used herein refers to molecules that do not comprising more than 4 repeating monomeric subunits.

The term "aromatic dialdehyde" as used herein refers to a compound comprising at least one aromatic moiety to which is bound to two aldehyde moieties arranged on the aromatic moiety such that they react with a compound comprising an amine moiety to form a conjugated product between the aromatic dialdehyde and the compound comprising an amine moiety.

The term "aromatic" as used herein refers to a chemical functional group that that contains a conjugated planar ring system with delocalized pi electron clouds instead of discrete alternating single and double bonds. In an embodiment, the aromatic group is phenyl or naphthyl.

The term "aliphatic dialdehyde" as used herein refers to an acyclic or cyclic aliphatic compound to which is bound to two aldehyde moieties arranged on aliphatic compound such that they react with a compound comprising an amine moiety to form a conjugated product between the aliphatic dialdehyde and the compound comprising an amine moiety.

The term "conjugating" as used herein means to bind two molecules together via a covalent linkage.

The term "pharmaceutically acceptable" as used herein means compatible with the treatment of subjects, in particular human subjects.

II. Methods of the Application

Methods of conjugating two molecules are disclosed herein in which a non-polymeric aliphatic dialdehyde or non-polymeric aromatic dialdehyde is reacted with a compound comprising an amine ($NH_2$) moiety to form a stable product under mild conditions. No side products are formed in the reaction that must be removed from the reaction mixture. The reaction does not require the use of catalysts or reducing agents.

The present application therefore includes a method for conjugating two molecules comprising reacting a non-polymeric aliphatic dialdehyde or non-polymeric aromatic dialdehyde with a compound comprising an $NH_2$ moiety under conditions for the conjugation of the $NH_2$ moiety with the dialdehyde to form a conjugated product. The method is performed in the absence of a reducing agent.

In the present application it has been shown that a conjugation method between an aldehyde and an amine is possible in the absence of reducing agents used in the prior art methods to reduce, and therefore presumably stabilize, the imine ad duct formed between the amine and the aldehyde. Further, contrary to prior art methods, polymeric dialdehyde compounds are also not needed to stabilize starting reagents and/or the resulting products.

Accordingly, the general nature of the present method would be understood by a person skilled in the art and, based on the results disclosed herein, it is clear that the method can be generally applied to a wide variety of molecular classes and tolerates many different functional groups. For example, the method has been shown to work for the conjugation of dyes, fluorophores, immunogenic moieties, targeting moieties, labeling reagents, metal complexes, lipids and carbohydrates to amine-containing compounds, such as proteins.

In an embodiment of the application the non-polymeric aliphatic dialdehyde is a compound of Formula I and the compound comprising an $NH_2$ moiety is selected from a compound of Formula II, III and IV, providing a conjugated product of the Formula V, VII and VII, respectively:

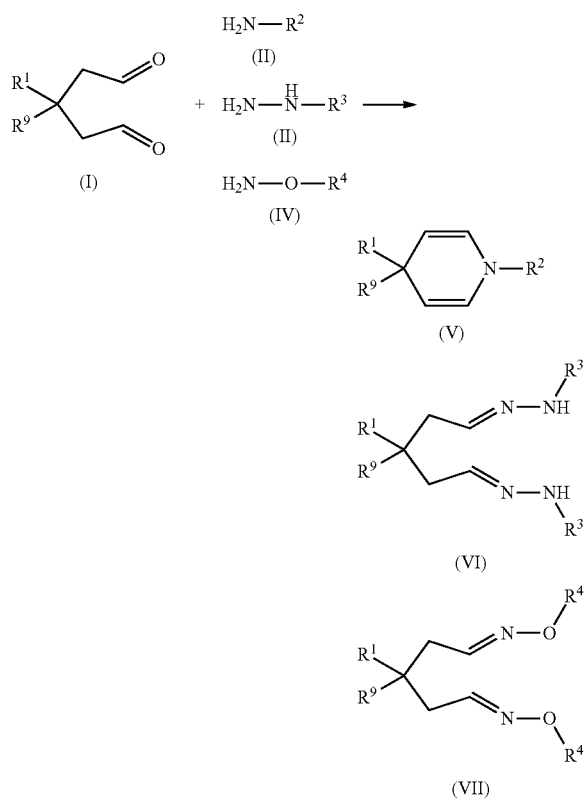

wherein:
$R^1$ is selected from a fluorescent dye, ligand, drug, small molecule, lipid, amino acid, dipeptide, tripeptide, monosaccharide, disaccharide, radiolabel, spin label, redox molecule, isotope label, PET label, nanoparticle, macrocycle, metal complex and Metal Organic Framework MOF, which are optionally linked to the $CH(CH_2)C(O)H$ via a linker moiety;
$R^2$, $R^3$ and $R^4$ are independently selected from a fluorophore, ligand, drug, small molecule, protein, lipid, carbohydrate, nucleic acid, peptide, dye, radiolabel, spin label, redox molecule, isotope label, PET label, nanoparticle, polymer, macrocycle, metal complex, solid support and MOF, which are optionally linked to the $NH_2$, $NH-NH_2$ or $O-NH_2$ via a linker moiety; and
$R^9$ is H or $C_{1-6}$alkyl.

In an embodiment, $R^1$ comprises a linker moiety. In an embodiment, the linker moiety is selected from $-(CH_2)_p-$, $-(CH_2)_{p'}-S-(CH_2)_p-$, $-(CH_2)_{p'}-O-(CH_2)_p-$, $-(CH_2)_{p'}-C(O)-(CH_2)_p-$, $-(CH_2)_{p'}-C(O)O-(CH_2)_p-$, $-(CH_2)_{p'}-OC(O)(CH_2)_p-$, $-(CH_2)_{p'}-C(O)NH-(CH_2)_p-$, $-(CH_2)_{p'}-NHC(O)-(CH_2)_p-$, $-(CH_2)_{p'}-OC(O)O-(CH_2)_p-$, $-(CH_2)_{p'}-OC(O)NH-(CH_2)_p-$, $-(CH_2)_{p'}-NHC(O)O-(CH_2)_p-$ and $O-(CH_2CH_2O)_p-$ wherein p and p' are independently selected from 0, 1, 2, 3, 4, 5, 6, 7, 8, 9 and 10. In a further embodiment, p and p' are independently selected from 0, 1, 2, 3, 4, 5 and 6. In yet a further embodiment, at least one of p and p' is other than 0.

In an embodiment, $R^1$ comprises a molecule selected from biotin, a cyanine dye, fluorescein, rhodamine, ferrocene, solid support, boron-dipyrromethene, 2,4-dinitrophenol (DNP), nitrobenzodioxazole (NBD), $N=C(CH_2C(O)H)_2$, monosaccharide linked to the dialdehyde moiety via a linker moiety and a $C_{1-10}$alkyl in which one or more $CH_2$ groups are optionally replaced by O, NR or S, wherein R is H or $C_{1-6}$alkyl and/or optionally substituted with aryl.

In an embodiment, $R^2$, $R^3$ and $R^4$ are independently selected from any biomolecule comprise an $NH_2$ moiety that reacts with the dialdehyde of Formula I. In an embodiment, $R^2$, $R^3$ and $R^4$ are independently a peptide or a protein. In a further embodiment, $R^2$, $R^3$ and $R^4$ are independently an antibody. In a further embodiment, $R^2$, $R^3$ and $R^4$ are independently a drug. In a further embodiment, $R^2$, $R^3$ and $R^4$ are independently a ligand. In a further embodiment, $R^2$, $R^3$ and $R^4$ are independently a solid support. In a further embodiment, $R^2$, $R^3$ and $R^4$, independently, do not comprise a linker moiety. In these embodiments, the method of the present application is used to incorporate a labeling moiety, targeting moiety, immunogenic moiety or binding moiety, for example a fluorescent moiety, a radiolabel, a spin label, a redox molecule, an isotope label, a PET label, a nanoparticle, biotin or a metal complex, into or onto the chemical structure of the peptide, protein, antibody, drug, ligand or solid support.

In an embodiment, $R^9$ is H or $C_{1-6}$alkyl. In another embodiment, $R^9$ is H or $C_{1-4}$alkyl. In a further embodiment, $R^9$ is selected from H, methyl, ethyl, propyl and butyl. In yet a further embodiment, $R^9$ H or methyl.

In an embodiment, the method comprises reacting a compound of Formula I with a compound of Formula II under conditions to provide a compound of Formula V.

Representative compounds of Formula I, wherein $R^1$ is a lipid, metal complex, fluorophore, ligand, carbohydrate and $C_{1-10}$alkyl in which at least one $CH_2$ is optionally replaced with NR, O or S and/or optionally substituted with aryl are shown in FIG. 1.

In another embodiment of the application, the aromatic dialdehyde is a compound of Formula VIII and the compound comprising an $NH_2$ moiety is selected from a compound of Formula IX, X and XI, providing a conjugated product of the Formula XII, XIII and XV, respectively

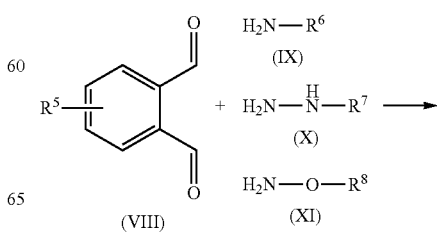

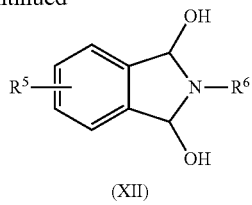

(XII)

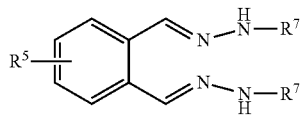

(XIII)

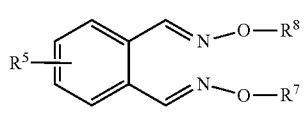

(XIV)

wherein:

$R_5$ is selected from a fluorescent dye, ligand, drug, small molecule, lipid, amino acid, dipeptide, tripeptide, monosaccharide, disaccharide, radiolabel, spin label, redox molecule, isotope label, PET label, nanoparticle, macrocycle, metal complex and MOF, which are optionally linked to the phenyl group via a linker moiety; and $R^6$, $R^7$ and $R^8$ are independently selected from a fluorophore, ligand, drug, small molecule, protein, lipid, carbohydrate, nucleic acid, peptide, dye, radiolabel, spin label, redox molecule, isotope label, PET label, nanoparticle, polymer, macrocycle, metal complex, solid support and MOF, which are optionally linked to the $NH_2$, $NH-NH_2$ or $O-NH_2$ via a linker moiety.

In an embodiment, $R^5$ comprises a linker moiety. In an embodiment, the linker moiety is selected from $-(CH_2)_p-$, $-(CH_2)_{p'}-S-(CH_2)_p-$, $-(CH_2)_{p'}-O-(CH_2)_p-$, $-(CH_2)_{p'}-C(O)-(CH_2)_p-$, $-(CH_2)_{p'}-C(O)O-(CH_2)_p-$, $-(CH_2)_{p'}-OC(O)(CH_2)_p-$, $-(CH_2)_{p'}-C(O)NH-(CH_2)_p-$, $-(CH_2)_{p'}-NHC(O)-(CH_2)_p-$, $-(CH_2)_{p'}-OC(O)O-(CH_2)_p-$, $-(CH_2)_{p'}-OC(O)NH-(CH_2)_p-$, $-(CH_2)_{p'}-NHC(O)O-(CH_2)_p-$ and $O-(CH_2CH_2O)_p-$ wherein p and p' are independently selected from 0, 1, 2, 3, 4, 5, 6, 7, 8, 9 and 10. In a further embodiment, p and p' are independently selected from 0, 1, 2, 3, 4, 5 and 6. In yet a further embodiment, at least one of p and p' is other than 0.

In an embodiment, $R^5$ comprises a molecule selected from biotin, a cyanine dye, fluorescein, rhodamine, ferrocene, solid support, boron-dipyrromethene, 2,4-dinitrophenol (DNP), nitrobenzodioxazole (NBD), $N=C(CH_2C(O)H)_2$ and a monosaccharide linked to the dialdehyde moiety via a linker moiety.

In an embodiment, $R^6$, $R^7$ and $R^8$ are independently selected from any biomolecule comprise an $NH_2$ moiety that reacts with the dialdehyde of Formula I. In an embodiment, $R^6$, $R^7$ and $R^8$ are independently a peptide or a protein. In a further embodiment, $R^6$, $R^7$ and $R^8$ are independently an antibody. In a further embodiment, $R^6$, $R^7$ and $R^8$ are independently a drug. In a further embodiment, $R^6$, $R^7$ and $R^8$ are independently a ligand. In a further embodiment, $R^6$, $R^7$ and $R^8$ are independently a solid support. In a further embodiment, $R^6$, $R^7$ and $R^8$, independently, do not comprise a linker moiety. In these embodiments, the method of the present application is used to incorporate a labeling moiety, targeting moiety, immunogenic moiety or binding moiety, for example a fluorescent moiety, a radiolabel, a spin label, a redox molecule, an isotope label, a PET label, a nanoparticle, biotin or a metal complex into or onto the chemical structure of the peptide, protein, antibody, drug, ligand or solid support.

In an embodiment, the method comprises reacting a compound of Formula VIII with a compound of Formula IX under conditions to provide a compound of Formula XII.

Figure 2:
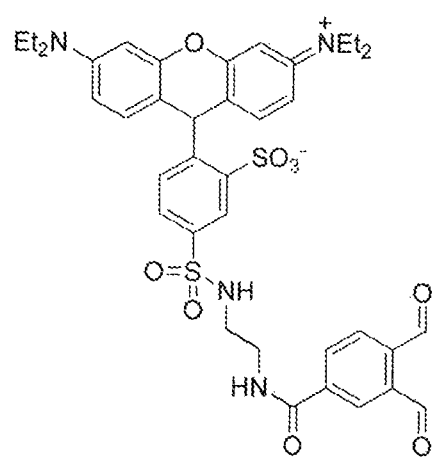
FIG. 2 shows a representative compound of Formula VIII, wherein R$^5$ is a fluorophore.

A representative compound of Formula VIII, wherein $R^5$ is a fluorophore is shown in FIG. 2.

In an embodiment, the conditions for the conjugation of the $NH_2$ moiety with the dialdehyde (for example, Formula I or Formula VIII) to form a conjugated product comprise combining aqueous solutions of the dialdehyde compound and the compound comprising an $NH_2$ moiety. In a further embodiment the aqueous solutions are combined for about 5 minutes to about 2 hours, or about 10 minutes to about 1 hour at a temperature in the range of about 5° C. to about 40° C., or about 10° C. to about 30° C. In an embodiment, an approximately 1:1 molar ratio of the $NH_2$ moiety and the dialdehyde are used. In an embodiment, the conjugation of the $NH_2$ moiety and the dialdehyde provides a conjugated product in a percent yield (based on molar amounts) of great than about 70%, 75%, 80%, 85%, 90% or 95%.

The resulting conjugated product may be isolated or purified using known methods, such as for example, lyophilization, chromatography, precipitation, filtration, microfluidic and liquid chromatography separation methods.

The dialdehyde moiety is incorporated into molecules using methods known in the art. As a representative example for the compounds of Formula I, the dialdehyde compounds are prepared as shown in Scheme 1:

Scheme 1

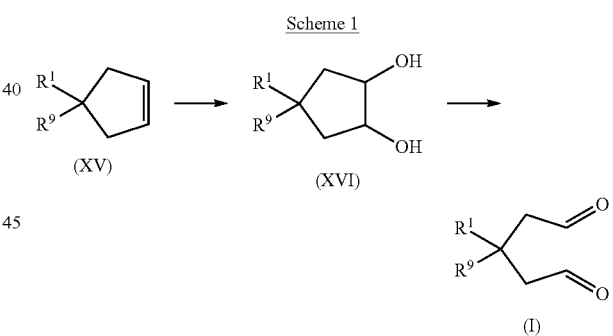

wherein $R^1$ and $R^9$ are as defined above.

Therefore a cyclopentene compound of Formula XV is treated under conditions of oxidative hydroxylation, followed by a further oxidation of the vicinal hydroxyl groups in the compounds of Formula XVI to provide compounds of Formula I. Exemplary reagents for the conversion of the compounds of Formula XV to compounds of Formula XVI include catalytic osmium tetraoxide and excess N-methylmorpholine N-oxide. Exemplary reagents for the conversion of the compounds of Formula XVI to compounds of Formula I include, sodium periodate. These methods are well-known in the art.

The aromatic dialdehyde moiety is incorporated into molecules using methods known in the art. As a representative example for the compounds of Formula VIII, the dialdehyde compounds are prepared as shown in Scheme 2:

Scheme 2

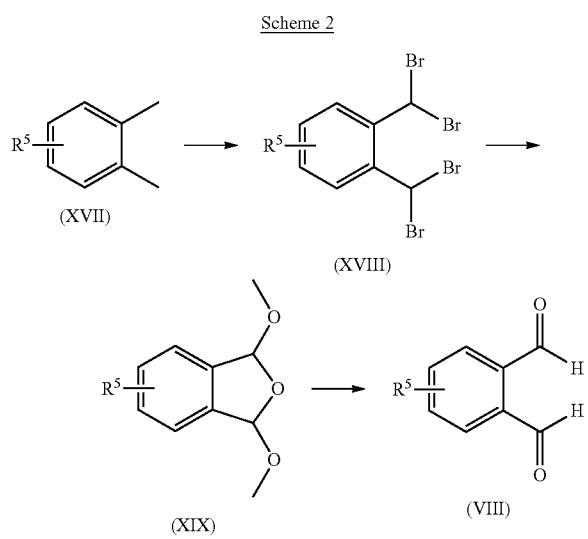

wherein R⁵ is as defined above.

Therefore aromatic dimethyl benzene of Formula XVII is treated with, for example, N-bromosuccinimide to generate brominated dimethyl groups. Replacement of the dibromomethyl groups with, for example, acidic methanol produces benzofuran XIX. The benzofuran of formula XIX is then ring opened with, for example, trifluoroacetic acid and water to produce the aromatic dialdehyde of Formula VIII. These methods are well-known in the art.

III. Compositions and Kits of the Application

Included in the present application are compositions and kits for conjugating molecules. In particular, the compositions and kits are for conjugating non-polymeric molecules to molecules comprising an $NH_2$ moiety.

In an embodiment, the non-polymeric molecule is selected from a labeling moiety, a binding moiety, a targeting moiety, and an immunogenic moiety.

In an embodiment, the present application includes compositions comprising a compound of Formula I wherein $R^1$ is selected from a fluorescent dye, ligand, drug, small molecule, lipid, amino acid, dipeptide, tripeptide, monosaccharide, disaccharide, radiolabel, spin label, redox molecule, isotope label, PET label, nanoparticle, macrocycle, metal complex and MOF, which are optionally linked to the $CH(CH_2)C(O)H$ via a linker moiety.

In an embodiment, $R^1$ comprises a linker moiety. In an embodiment, the linker moiety is selected from —$(CH_2)_p$—, —$(CH_2)_{p'}$—S—$(CH_2)_p$—, —$(CH_2)_{p'}$—O—$(CH_2)_p$—, —$(CH_2)_{p'}$—C(O)—$(CH_2)_p$—, —$(CH_2)_{p'}$—C(O)O—$(CH_2)_p$—, —$(CH_2)_{p'}$—OC(O)$(CH_2)_p$—, —$(CH_2)_{p'}$—C(O)NH—$(CH_2)_p$—, —$(CH_2)_{p'}$—NHC(O)—$(CH_2)_p$—, —$(CH_2)_{p'}$—OC(O)O—$(CH_2)_p$—, —$(CH_2)_{p'}$—OC(O)NH—$(CH_2)_p$—, —$(CH_2)_{p'}$—NHC(O)O—$(CH_2)_p$— and O—$(CH_2CH_2O)_p$— wherein p and p' are independently selected from 0, 1, 2, 3, 4, 5, 6, 7, 8, 9 and 10. In a further embodiment, p and p' are independently selected from 0, 1, 2, 3, 4, 5 and 6. In yet a further embodiment, at least one of p and p' is other than 0.

In an embodiment, $R^1$ comprises a molecule selected from biotin, a cyanine dye, fluorescein, rhodamine, ferrocene, solid support, boron-dipyrromethene, 2,4-dinitrophenol (DNP), nitrobenzodioxazole (NBD), $N=C(CH_2C(O)H)_2$, a monosaccharide linked to the dialdehyde moiety via a linker moiety and a $C_{1-10}$alkyl in which one or more $CH_2$ groups are optionally replaced by O, NR or S, wherein R is H or $C_{1-6}$alkyl and/or optionally substituted with aryl.

In an embodiment, the present application includes compositions comprising a compound of Formula VIII wherein $R^5$ is selected from a fluorescent dye, ligand, drug, small molecule, lipid, amino acid, dipeptide, tripeptide, monosaccharide, disaccharide, radiolabel, spin label, redox molecule, isotope label, PET label, nanoparticle, macrocycle, metal complex and MOF, which are optionally linked to the phenyl group via a linker moiety.

In an embodiment, $R^5$ comprises a linker moiety. In an embodiment, the linker moiety is selected from —$(CH_2)_p$—, —$(CH_2)_{p'}$—S—$(CH_2)_p$—, —$(CH_2)_{p'}$—O—$(CH_2)_p$—, —$(CH_2)_{p'}$—C(O)—$(CH_2)_p$—, —$(CH_2)_{p'}$—C(O)O—$(CH_2)_p$—, —$(CH_2)_{p'}$—OC(O)$(CH_2)_p$—, —$(CH_2)_{p'}$—C(O)NH—$(CH_2)_p$—, —$(CH_2)_{p'}$—NHC(O)—$(CH_2)_p$—, —$(CH_2)_{p'}$—OC(O)O—$(CH_2)_p$—, —$(CH_2)_{p'}$—OC(O)NH—$(CH_2)_p$—, —$(CH_2)_{p'}$—NHC(O)O—$(CH_2)_p$— and O—$(CH_2CH_2O)_p$— wherein p and p' are independently selected from 0, 1, 2, 3, 4, 5, 6, 7, 8, 9 and 10. In a further embodiment, p and p' are independently selected from 0, 1, 2, 3, 4, 5 and 6. In yet a further embodiment, at least one of p and p' is other than 0.

In an embodiment, $R^5$ comprises a molecule selected from biotin, a cyanine dye, fluorescein, rhodamine, ferrocene, solid support, boron-dipyrromethene, 2,4-dinitrophenol (DNP), nitrobenzodioxazole (NBD), $N=C(CH_2C(O)H)_2$ and a monosaccharide linked to the dialdehyde moiety via a linker moiety.

In an embodiment, the composition comprising a compound of the Formula I or VIII further comprises water. In a further embodiment, the composition comprising a compound of the Formula I or VIII further comprises an aqueous buffer.

In an embodiment of the present application, there is included kits for conjugation of labeling moieties to molecules comprising an $NH_2$ moiety, for example, for labeling antibodies, proteins, peptides, ligands, synthetic oligonucleotides and other biomolecules for use, for example, with immunochemistry, fluorescence in situ hybridization (FISH), cell tracing, receptor labeling, and cytochemistry applications as well as probing biological structure, function and interactions. In a further embodiment, the kits are for conjugation of biotin and other haptens to biomolecules.

In an embodiment, the kits of the present application comprise a compound of Formula I or a compound of Formula VIII, and, optionally, instructions for use, buffers, purification reagents and/or purification tools. Examples of purification reagents and tools include, for example, one or more of purification resins, columns, funnels, column holders, disposable pipets and collections tubes.

The present application also includes compositions and kits comprising the conjugated product. In an embodiment, the compositions comprising the conjugated product are for in vitro use. In an embodiment, the compositions comprising the conjugated product are for in vivo use and therefore are pharmaceutically acceptable.

In an embodiment, the present application includes a composition comprising a compound selected from a compound of Formula V, VI, VII, XII, XIII and XIV and a carrier. In an embodiment, the composition is a pharmaceutical composition and the carrier is a pharmaceutically acceptable carrier.

The pharmaceutical compositions of the present application are administered to a subject in a variety of forms depending on the selected route of administration, as will be understood by those skilled in the art. A pharmaceutical composition of the present application is, for example, administered, for example, by oral, parenteral, buccal, sublingual, nasal, rectal, patch, pump or transdermal administration and the pharmaceutical composition formulated accordingly.

Parenteral administration includes intravenous, intraperitoneal, subcutaneous, intramuscular, transepithelial, nasal, intrapulmonary, intrathecal, rectal and topical modes of administration. In an embodiment, parenteral administration is by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

It is also possible to freeze-dry the compositions of the present application and use the lyophilizates obtained, for example, for the preparation of products for injection.

The pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringability exists.

EXAMPLES

The following non-limiting examples are illustrative of the present application:

Example 1

Preparation of Lipid-Containing Compound of Formula I (a) Diethyl cyclopent-3-ene-1, 1 -dicarboxylate

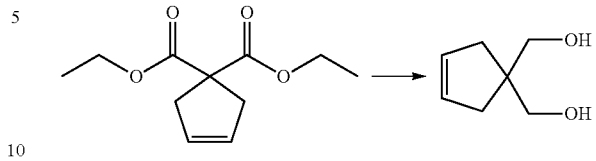

To a solution of diethyl malonate (2.00g, 12.48mmol) in 50 ml t-butanol and metallic Na (0.287 g, 12.48 mmol) was added cis-1, 4-dichlorobut-2-ene. The mixture was stirred until a yellow solution was obtained, only then another portion of (0.287 g, 12.48 mmol metallic Na) was added and stirred for 12 h. t-Butanol was distilled off under vacuum and the mixture was diluted with DCM. The organic solution was filtered and washed with H$_2$O (6×50 mL), saturated NH$_4$Cl (3×50 mL), and H$_2$O (2×50 ml), dried over MgSO$_4$, and purified with silica Hex:EtOAc (2:8) to afford a clear oil solid (11.23 mmol, 90%). $^1$H NMR (400 MHz, CDCl$_3$): δ 1.24-1.28; (t, 6 H, J=7.16Hz), 3.02; (s, 4H,), 4.20-4.22; (q, 4H, J=7.7 Hz), 5.59; (s, 2H).

(b) cyclopent-3-ene-1,1 -diyldimethanol

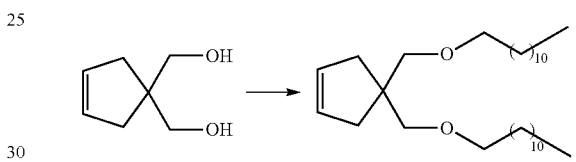

To a suspension of lithium aluminum hydride (1.706 g, 44.92 mmol) in dry 100 ml THF at −78° C., diethyl cyclopent-3-ene-1,1 -dicarboxylate (Example 1(a), 2.38 g, 11.23 mmol) was added drop wise over 1 h. The mixture was stirred for 5 h, and then quenched with 15 ml 1M NaOH. The mixture was stirred for an additional 2 h, then concentrated and up taken in diethyl ether and dried over MgSO$_4$ to afford white solid (9.54 mmol, 85%). $^1$H NMR (300 MHz, CDCl$_3$): δ 2.23-2.26; (m, 4H). 3.65; (d,4H, J=5.14 Hz), 5.65; (s, 2H).

(c) 4,4-bis(dodecyloxymethyl)cyclopent-1-ene

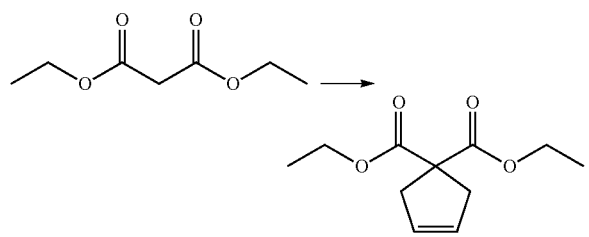

To a suspension of excess NaH in dry 100 ml dry THF at −78° C. was added cyclopent-3-ene-1,1-diyldimethanol (Example 1(b), 1.222 g, 9.54 mmol) and stirred for 1 h. Temperature was gradually increased to −40 ° C. and bromododecane (7.104 g, 28.62 mmol) was added drop wise over 0.5h. The mixture was mildly refluxed overnight. THF was distilled off under vacuum and the mixture was diluted with DCM. The organic solution was filtered and washed with H$_2$O (6×50 ml), saturated NH$_4$Cl (3×50 mL), and H$_2$O (2×50 ml,), dried over MgSO$_4$, and purified with silica Hex:EtOAc (2:8) to afford a clear oil solid (7.60 mmol, 80%). $^1$H NMR (700 MHz, CDCl$_3$): δ 0.89-0.91; (t, 6H, J=7.10 Hz), 1.20; (m, 20H), 1.55-1.58; (m, 4H), 2.20; (s, 4H), 3.33; (s, 4H), 3.42-3.44 (t, 4H, J=6.66 Hz), 5.6; (s, 2H).

(d) 4,4-bis(dodecyloxymethyl)cyclopenl-1-ene-1,2-diol

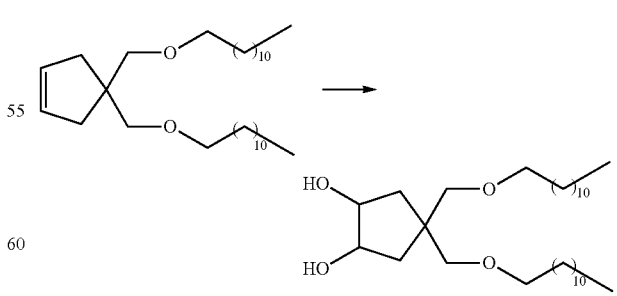

To a solution of 4,4-bis(dodecyloxymethyl)cyclopent-1-ene (Exmaple 1(c), 3.541 g, 7.60 mmol) in acetone: acetonitrile (1:1) was added catalytic amount of OsO$_4$ and excess N-methylmorpholine N-oxide 50% in H$_2$O. The reaction was monitored by TLC for complete disappearance of starting material. Solvent was distilled off under vacuum and the product was taken into diethyl ether and dried over MgSO$_4$, and further purified with silica Hex:EtOAc (3:7) to afford a white solid (6.84 mmol, 90%). $^1$H NMR (700 MHz, CDCl$_3$): δ 0.89-0.91; (t, 6H, J=14.15 Hz), 1.52-1.56; (qn, 2H, J=6.96 Hz), 1.61-1.65; (qn, 2H, J=7.21 Hz), 1.67-1.70; (dd, 2H, J=14.17, 5.06 Hz), 1.84-1.87; (dd,2H, J=14.14, 6.36 Hz), 3.15; (s, 2H), 3.29; (s, 2H), 3.37-3.39; (t, 4H, J=6.57 Hz), 3.51-3.53; (t, 4H, J=6.68 Hz), 3.91-3.95; (dt, 2H, J=8.73, 4.13 Hz).

(e) 3,3-bis(dodecyloxymelhyl)pentanedial

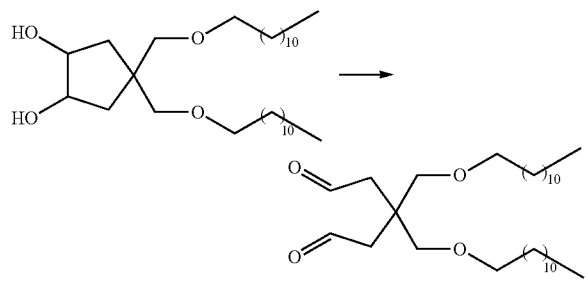

To a solution of 4,4-bis(dodecyloxymethyl)cyclopent-1-ene-1,2-diol (Example 1(d), 3.392 g, 6.84 mmol) in H$_2$O:methanol (1:9) was added NaIO$_4$ (1.456 g, 6.84 mmol). The reaction was monitored by TLC for complete disappearance of starting material. The solvent was distilled off under vacuum and the product was taken into diethyl ether and dried over MgSO$_4$, and further purified with silica Hex:EtOAc (3:7) to afford a white solid (6.84 mmol, 90%). $^1$H NMR (300 MHz, CDCl$_3$): δ 7.76; (d, 4H, J=8.4 Hz), 7.38; (d,4H, J=7.7 Hz), 4.11-4.07; (m, 4H), 3.63-3.58; (m 4 H), 2.45; (s, 6H).

Example 2

Preparation of 2,4-dinitrophenyl-Containing Compound of Formula I (a) N1-(2,4-dinitrophenyl)octane-1,8-diamine

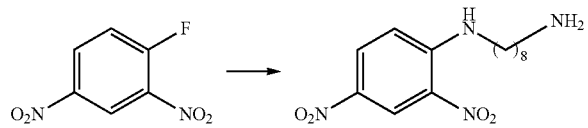

To a solution of 1-fluoro-2,4-dinitrobenzene (2.00 g, 12.48 mmol) in 1 ml THF:H$_2$O (2:1) and NaHCO$_3$ (0.287 g, 12.48 mmol) was slowly added a dilute solution of octane-1,8-diamine in THF over 2h at rt. The mixture was stirred for 12 h, solvent was distilled off under vacuum and the mixture was diluted with DCM. The organic solution was filtered and washed with H$_2$O (6×50 mL), saturated NH$_4$Cl (3×50 mL), and H$_2$O (2×50 mL), dried over MgSO$_4$, and purified with silica Hex:EtOAc (5:5) to afford a yellow thick oil (11.23 mmol, 90%). $^1$H NMR (700 MHz, MeOD): δ 9.05; (s, 1H), 8.31-8.30; (d, 1H, J=7.7 Hz), 7.18; (s, 1H), 3.61-3.41; (t, 2 H), 2.74-2.64; (t, 2 H), 1.78-1.77; (q, 4 H), 1.56-1.54; (q, 2 H), 1.50-1.48; (q, 2 H), 1.41-1.40; (m, 2 H, J).

(b) N-(8-(2,4-dinitrophenylamino)octyl)cyclopent-3-enecarboxamide

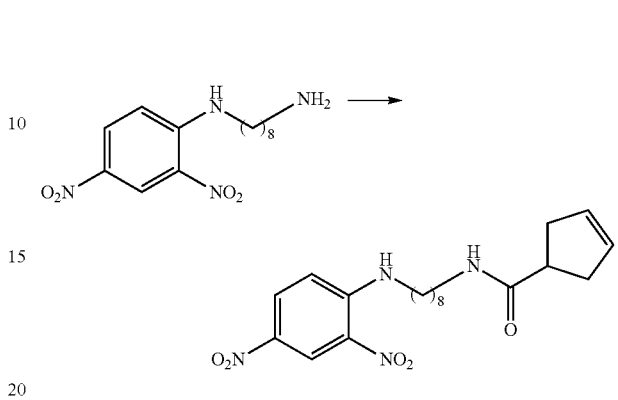

To a solution of N1-(2,4-dinitrophenyl)octane-1,8-diamine (Exmaple, 2(a), 2.00 g, 12.48 mmol) in 10 ml THF:H$_2$O (9:1) and NaHCO$_3$ (0.287 g, 12.48 mmol) was slowly added 2-(cyclopent-3-enecarbonyloxyamino)cyclopentane-1,3-dione in THF over 2 h at rt. The mixture was stirred for 12 h. Solvent was distilled off under vacuum and the mixture was diluted with DCM. The organic solution was filtered and washed with H$_2$O (6×50 mL), saturated NH$_4$Cl (3×50 mL), and H$_2$O (2×50 mL), dried over MgSO$_4$, and purified with silica MeOH:DCM (5:95) to afford a yellow thick solid (11.23mmol, 90%). $^1$H NMR (700 MHz, MeOD): δ 9.05; (s, 1H), 8.31-8.30; (d, 1H, J=7.7 Hz), 7.18; (s, 1H), 4.13-4.12; (q, 2 H), 3.51-3.41; (q, 2 H), 3.16-3.14; (t, 2 H,), 2.01; (q, 1H), 1.95-1.92; (q, 2 H), 1.89-1.77; (q, 2 H), 1.78-1.75; (q, 2 H), 1.51-1.48; (q, 2 H), 1.38-1.35; (m, 2 H).

(c) N-(8-(2,4-dinitrophenylamino)octyl)-3,4-dihydroxycyclopentanecarboxamide

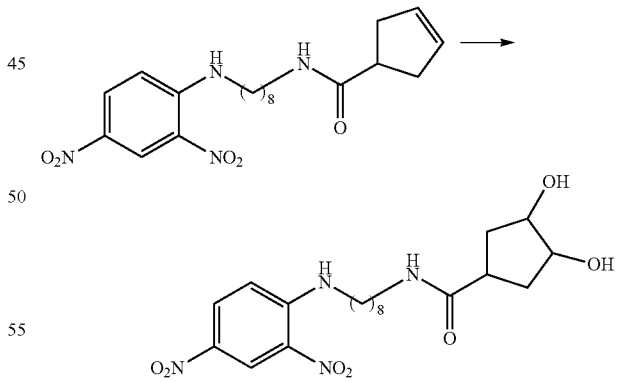

To a solution of N-(8-(2,4-dinitrophenylamino)octyl)cyclopent-3-enecarboxamide (Example 2(b), 2.00 g, 12.48 mmol) in 10 ml ACN:Acetone:H$_2$O (4:4:2) was slowly added catalytic amount of OsO$_4$ and excess N-methylmorpholine N-oxide 50% in H$_2$O. The solvent was distilled off under vacuum and the mixture was diluted with DCM. The organic solution was filtered and washed with H$_2$O (6×50 mL), saturated NH$_4$Cl (3×50 mL), and H$_2$O (2×50 mL), dried over MgSO$_4$, and purified with silica MeOH:DCM (5:95) to afford a yellow thick solid (11.23 mmol, 90%). $^1$H NMR (700 MHz, MeOD): δ 9.05; (s, 1H), 8.31-8.30; (d, 1H, J=7.7 Hz), 7.18; (s, 1H), 4.13-4.12; (q, 2 H), 3.51-3.41; (q, 2 H), 3.16-3.14; (t, 2 H), 2.01; (q, 1H), 1.95-1.92; (q, 2 H,), 1.89-1.77; (q, 2 H), 1.78-1.75; (q, 2 H), 1.51-1.48; (q, 2 H), 1.38-1.35; (m, 2 H).

(d) N-(8-(2,4-dinitrophenylamino)octyl)-4-oxo-2-(2-oxoethyl)butanamide

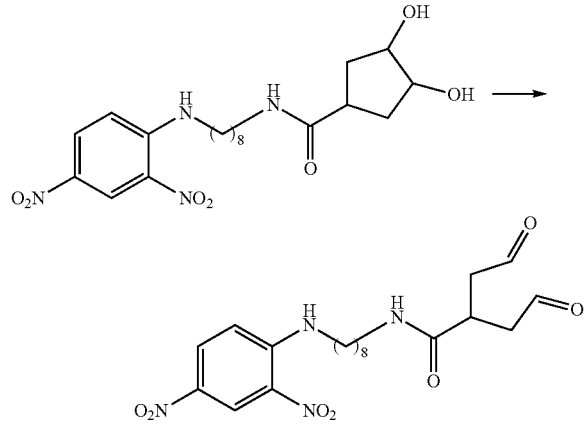

To a solution of N-(8-(2,4-dinitrophenylamino)octyl)-3,4-dihydroxycyclopentanecarboxamide (Example 2(c), 3.392 g, 6.84 mmol) in H$_2$O:methanol (1:9) was added 1.1 eq NaIO$_4$ (1.456 g, 6.84 mmol). The reaction was monitored by TLC for complete disappearance of starting material. Solvent was distilled off under vacuum and the product was taken into diethyl ether and dried over MgSO$_4$, and further purified with silica Hex:EtOAc (3:7) to afford a white solid (6.84 mmol, 90%). $^1$H NMR (700 MHz, MeOD): δ 9.05; (s, 1H), 8.31-8.30; (d, 1H, J=7.7 Hz), 7.18; (s, 1H), 4.13-4.12; (q, 2 H), 3.51-3.41; (q, 2 H), 3.16-3.14; (t, 2 H), 2.01; (q, 1H), 1.95-1.92; (q, 2 H), 1.89-1.77; (q, 2 H), 1.78-1.75; (q, 2 H), 1.51-1.48; (q, 2 H), 1.38-1.35; (m, 2 H).

Example 3

Preparation of Biotin-Containing Compound of Formula I (a) Biotin Cyclopentene

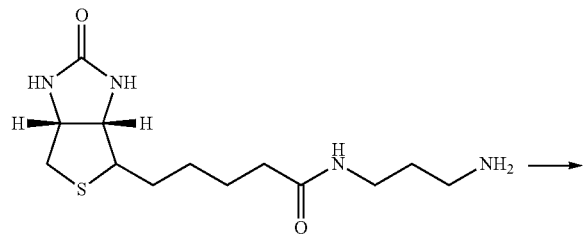

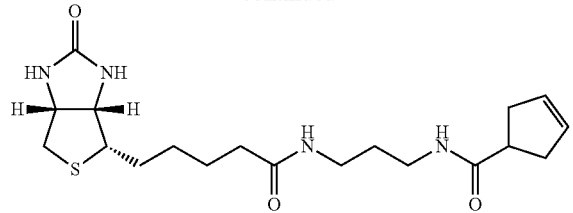

To a solution of N-(+)-biotinyl-3-aminopropylammonium trifluoroacetate (2.00 g, 12.48 mmol) in 10 ml THF:H$_2$O (5:5) and excess NaHCO$_3$ was slowly added 2-(cyclopent-3-enecarbonyloxyamino)cyclopentane-1,3-dione in THF over 6h at rt. Solvent was distilled off under vacuum and the product purified with silica MeOH:DCM (10:90) to afford a white solid (11.23 mmol, 90%). $^1$H NMR (700 MHz, MeOD): δ 5.67; (s, 2H), 4.50-4.46; (dd, 1H, J=7.7 Hz), 4.33-4.32; (dd, 2H), 3.23-3.19; (m, 4 H), 3.1-3.80; (q, 1 H), 2.93-2.92; (dd, 1 H), 2.73-2.71; (dd, 1H), 2.73-2.63; (m, 3 H), 2.23-2.22; (t, 2 H), 1.76-1.62; (m, 2 H), 1.46-1.45; (q, 2 H).

(b) Biotin cyclopandiol

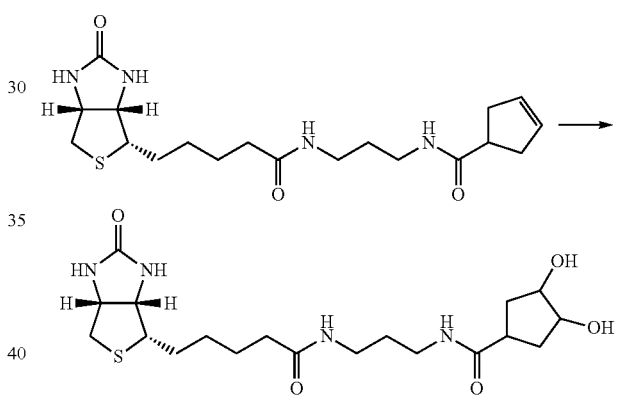

To a solution of biotin cyclopentene (Example 3(a), 2.00g, 12.48mmol) in 10 ml ACN:Acetone:H$_2$O (4:4:2) was slowly added catalytic amount of OsO$_4$ and excess N-Methylmorpholine A-oxide 50% in H$_2$O. The solvent was distilled off under vacuum and the product purified with flash chromatography silica MeOH:DCM (10:90) to afford a white solid (11.23 mmol, 90%). $^1$H NMR (700 MHz, MeOD): δ 9.05; (s, 1H), 8.31-8.30; (d, 1H, J=7.7 Hz), 7.18; (s, 1H), 4.13-4.12; (q, 2 H), 3.51-3.41; (q, 2 H), 3.16-3.14; (t, 2 H), 2.01; (q, 1H), 1.95-1.92; (q, 2 H), 1.89-1.77; (q, 2 H), 1.78-1.75; (q, 2 H), 1.51-1.48; (q, 2H), 1.38-1.35; (m, 2 H).

(c) Biotin dialdehyde

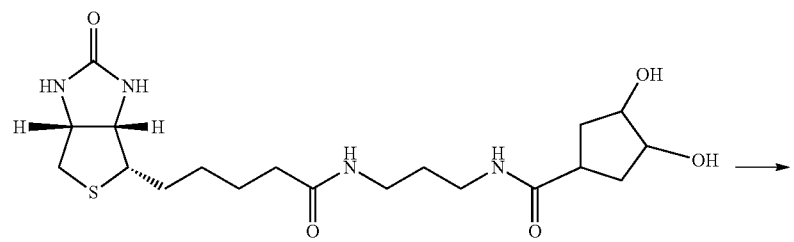

-continued

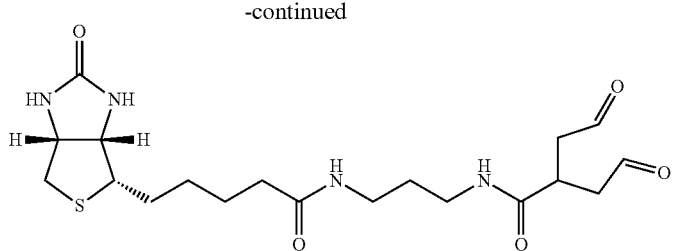

To a solution of biotin cyclopandiol (Example 3(b), 3.392 g, 6.84 mmol) in H₂O:methanol (1:9) was added 1.1 eq NaIO₄ (1.456 g, 6.84 mmol). The reaction was monitored by TLC for complete disappearance of starting material. The solvent was distilled off under vacuum and the product was taken into diethyl ether and dried over MgSO₄, further purified with MeOH:DCM (10:90) to afford a white solid (6.84 mmol, 90%) ¹H NMR (700 MHz, MeOD): δ 9.05; (s, 1H), 8.31-8.30; (d, 1H, J=7.7 Hz), 7.18; (s, 1H), 4.13-4.12; (q, 2 H), 3.51-3.41; (q, 2 H), 3.16-3.14; (t, 2 H), 2.01; (q, 1H), 1.95-1.92; (q, 2 H), 1.89-1.77; (q, 2 H), 1.78-1.75; (q, 2 H), 1.51-1.48; (q, 2 H), 1.38-1.35; (m, 2 H).

Example 4

Preparation of Small Molecule-Containing Compound of Formula I (a) 2,5-dioxopyrrolidin-1-yl cyclopent-3-enecarboxylate

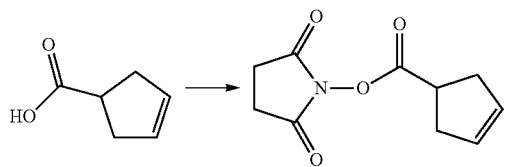 [SMILES: O=C(O)C1CC=CC1 ; O=C(ON1C(=O)CCC1=O)C1CC=CC1]

3-Cyclopentenecarboxylic acid (0.5000 g, 4.45 mmol), N,N'-methanetetraylbis[cyclohexanamine] (1.104 g, 5.35 mmol, 1.2 eq) and N-hydroxysuccinimide (0.6206 g, 5.35 mmol, 1.2 eq) were all mixed in a 50 ml dry DCM and stirred for 6 h. DCM was distilled off under vacuum and the mixture was purified with silica Hex:EtOAc (2:8) to afford a white solid (2.60 mmol, MW 209.20 g/mol, 58%). ¹H NMR (300 MHz, CDCl₃): δ 1.58; (s), 2.19; (s), 2.83; (s), 2.85; (s), 3.49-3.39; m, 5.71; (s).

(b) N-propylcyclopent-3-enecarboxamide

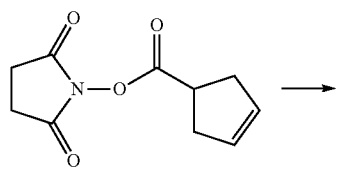

-continued

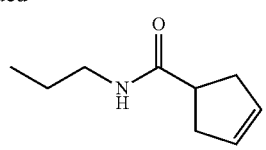

To a solution of 2,5-dioxopyrrolidin-1-yl cyclopent-3-enecarboxylate (0.5439 g, 2.60 mmol) in dry DCM was added large excess of propyl amine (0.780 g, 0.013 mmol). Mixture was stirred for 1 h, then concentrated and flushed through a pad of silica to afford white solid (2.34 mmol, MW 153.22 g/mol, 95%). ¹H NMR: molecule was not purified as isolated product.

(c) 3,4-dihydroxy-N-propylcyclopentanecarboxamide

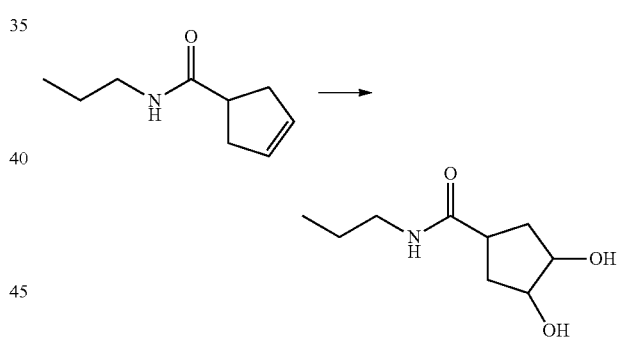

To a solution of N-propylcyclopent-3-enecarboxamide (0.3585 g, 2.34 mmol) in acetone: acetonitrile (1:1) was added catalytic amount of OsO₄ and excess N-Methylmorpholine N-oxide 50% in H₂O. Reaction was monitored with TLC for complete disappearance of starting material. Solvent was distilled off under vacuum and the product was taken into diethyl ether and dried over MgSO₄, further two separate diastereomers were purified with silica Hex:EtOAc (3:7) to afford white solid (2.106 mmol, MW 187.24 g/mol, 90%). ¹H NMR (700 MHz, MeOD): Isomer (3R,4S) δ 0.94; (t, 3H, J=7.3 Hz), 1.53; (sextet, 2H, J=7.2 Hz), 1.83-1.79; (dddt, 2H), 2.16-2.11; (dddt, 2H), 2.76-2.71; (tt, 1H, J=9.27, 6.46 Hz), 3.14; (t, 2H, J=7.07 Hz), 3.96-3.94; (m, 2H). Isomer (3S,4R): %) ¹H NMR (700 MHz, MeOD): Isomer (3R,4S) δ 0.93; (t, 3H, J=7.43 Hz), 1.54-1.49; (sextet, 2H, J=7.23 Hz), 1.91-1.87; (dddt, 2H), 1.97-1.93; (dddt, 2 H), 3.02-3.00; (tt, 1 H), 3.12; (t, 2H, J 7.10 Hz), 4.13-4.11; (m, 2H).

(d) 4-oxo-2-(2-oxoethyl)-N-propylbulcmamide

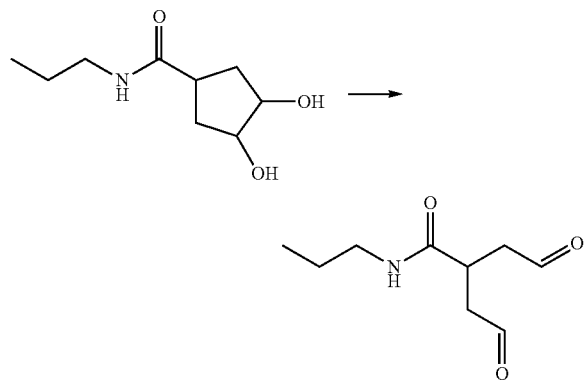

To a solution of 3,4-dihydroxy-N-propylcyclopentanecarboxamide (0.3940 g, 2.106 mmol) in H₂O:methanol (1:9) was added NaIO₄ (0.4504 g, 2.106 mmol). Mixture was stirred for 1 h until a flakey white, solid iodate salt, was obtained. Solvent was distilled off under vacuum and the product was taken into diethyl ether and dried over MgSO₄ and used for subsequent reactions. The clear oil could not be purified using any conventional chromatographic systems. ¹H NMR: molecule was not purified as isolated product.

Example 5

Preparation of Small Molecule-Containing Compound of Formula I (a) N-phenethylcyclopent-3-enecarboxamide

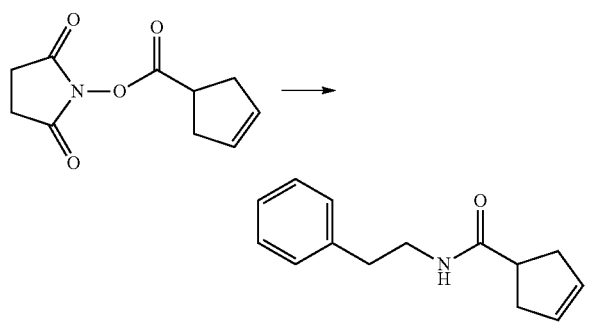

To a solution of 2,5-dioxopyrrolidin-1-yl cyclopent-3-enecarboxylate (0.04162 g, 0.198 mmol) in water and sodium bicarbonate (excess) was added phenethylamine (0.0221 g, 0.1824 mmol, 1.1 eq). Mixture was stirred for 1 h, then concentrated and flushed through a pad of silica to afford white solid (0.165 mmol, MW 215.29 g/mol). ¹H NMR: molecule was not purified as isolated product. ¹H NMR (400 MHz, CDCl₃): δ 2.59-2.59; (dd, 4H), 2.83-2.85; (t, 2H, J=6.9 Hz), 2.87-2.91; (tt, 1H), 3.54-3.57; (td,2H, 6.88, 5.97 Hz), 5.67-5.68; (m,2H, 2.28 Hz), 7.20-7.22; (m), 7.27-7.27; (tt, 1H,), 7.32-7.35; (m).

(b) 3,4-dihydroxy-N-phenethylcyclopentanecarboxamide

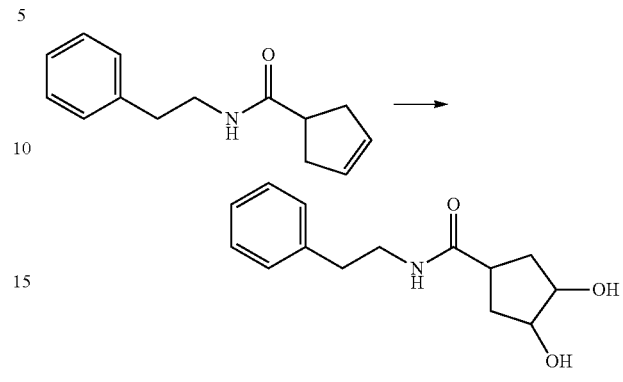

To a solution of N-phenethylcyclopent-3-enecarboxamide (approximately 0.198 mmol) in acetone: acetonitrile (1:1) was added catalytic amount of OsO₄ and excess N-Methylmorpholine N-oxide 50% in H₂O. Reaction was monitored with TLC for complete disappearance of starting material. Solvent was distilled off under vacuum and the product was taken into diethyl ether and dried over MgSO₄, further the product was isolated only as an impure crude mixture of two diastereomers as white solid (MW 249.31 g/mol). ¹H NMR (400 MHz, CDCl₃): Mixture of Isomers (3R,4S)/(3S,4R): δ 1.88-1.92; (dddt, 2H, J=13.81, 9.38, 4.32 Hz), 2.04-2.07; (dddt, 2H), 2.81-2.83; (t, 2H, J=13.78 Hz), 3.84-3.89; (tt, 1H), 3.51-3.54; (t,2H), 4.24-4.25; (m,1H), 4.29-4.46; (dt, 1H) 7.20-7.22; (m), 7.27-7.27; (tt, 1H,), 7.32-7.35; (m).

(c) N-benzyl-4-oxo-2-(2-oxoethyl)butanamide

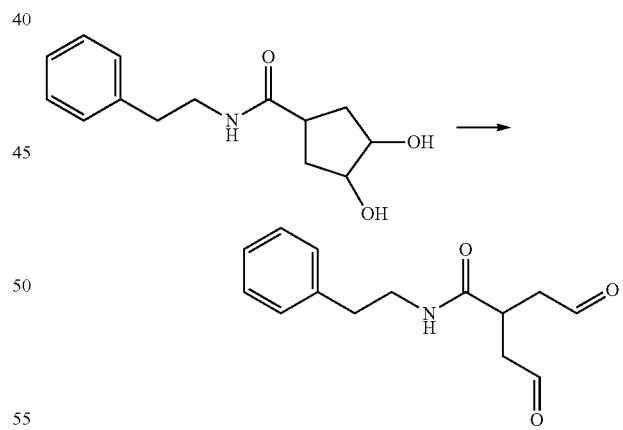

To a solution of 3,4-dihydroxy-N-phenethylcyclopentanecarboxamide in H₂O:methanol (1:9) was added NaIO₄. Mixture was stirred for 1 h until a flakey white, solid iodate salt, was obtained. Solvent was distilled off under vacuum and the product was taken into diethyl ether and dried over MgSO₄ and used for subsequent reactions. The clear oil could not be purified using any conventional chromatographic systems. Product was estimated to be <20 mg (crude yield). ¹H NMR: molecule was not purified as isolated product.

Example 6

Preparation of Small Molecule-Containing Compound of Formula I (a) 1-methylcyclopent-3-enecarboxylic acid

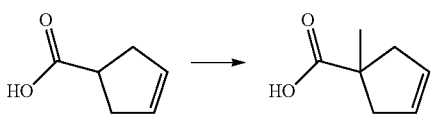

To a solution of cyclopent-3-enecarboxylic acid (0.5000, 4.459 mmol) in 50 mL dry THF at −78° C. under inert atmosphere was added t-butyl lithium 1.7M (9 ml, 13.37 mmol, 3 eq) over 1 h. The mixture was stirred at the same temperature for an additional 30 minutes until dianion was successfully generated, then excess iodomethane was added gently. A white precipitate forms to produce a suspension which dissolves at higher temperature overnight. The mixture was quenched by 1 ml of $H_2O$ and stirred for 15 min, then THF was stripped off under vacuum and the remaining crude mixture was diluted with DCM. The organic solution was filtered and washed with $H_2O$ (6×50 mL), saturated $NH_4Cl$ (3×50 mL), and $H_2O$ (2×50 mL), dried over $MgSO_4$, and purified with silica Hex:EtOAc (2:8) to afford a clear oil solid (3.121 mmol, MW 126.15 g/mol, 70%), repeating the experiment on the crude will yield 100% product, $^1H$ NMR (700 MHz, $CDCl_3$): δ 1.362; (s, 3H) , 2.27-2.29; (d, 2H, J=14.82 Hz), 2.96-2.98; (d, 2H, J=14.69 Hz), 5.64; (s, 2H).

(b) 3,4-dihydroxy-1-methylcyclopentanecarboxylic acid

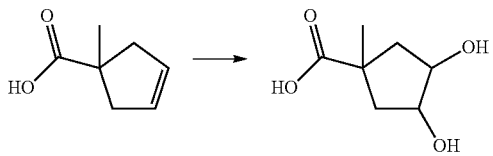

To a solution of 1-methylcyclopent-3-enecarboxylic acid (0.5000 g, 4.459 mmol) in acetone: acetonitrile (1:1) was added catalytic amount of $OsO_4$ and excess N-Methylmorpholine N-oxide 50% in $H_2O$. Reaction was monitored with TLC for complete disappearance of starting material. Solvent was distilled off under vacuum and the product was taken into ethyl acetate and dried over $MgSO_4$, further purified with silica MeOH:EtOAc (0.5:9.5) to afford a white solid (3.121 mmol, MW 160.17 g/mol, 70%). $^1H$ NMR (400 MHz, MeOD): δ 1.392; (s, 3H), 1.632-1.663; (dd, 2H), 2.37-2.40; (dd, 2H), 4.054; (dt, 2H).

(c) 2,2,5-trimethyltetrahydro-3aH-cyclopenla[d][1,3] dioxole-5-carboxylic acid

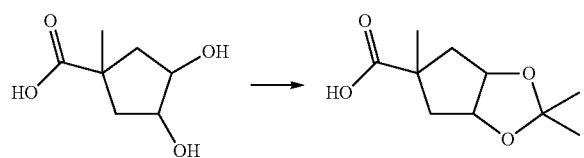

To a solution of 3,4-dihydroxy-1-methylcyclopentanecarboxylic acid (0.5000, 3.121 mmol) in dry THF and catalytic amount of p-TsOH was added large excess of 2,2-dimethoxypropane. Reaction was monitored with TLC for complete disappearance of starting material. THF was distilled off under vacuum and the mixture was diluted with DCM. The organic solution was filtered and washed with $H_2O$ (2×50 mL), dried over $MgSO_4$, and purified with silica Hex:EtOAc (7:3) to afford mixture of diastereomers as white solid (2.964 mmol, MW 200.23 g/mol, 95%). $^1H$ NMR (700 MHz, $CDCl_3$): δ 1.28-1.39; (4s, 12H), 1.518; (s, 3H), 1.540; (s, 3H), 1.92-1.95; (d, 2H, J=14.59 Hz), 2.28-2.30; (d, 2H), 2.68-2.70; (d, 2H, J=14.51 Hz), 4.682-4.689; (d, 1H , J=4.38 Hz), 4.760-4.769; (d, 1H).

(d) 1H-benzo[d][1,2,3]triazol-1-yl-2,2,5-trimethyl-tetrahydro-3aH-cyclopenta[d][1,3]dioxole-5-carboxylate

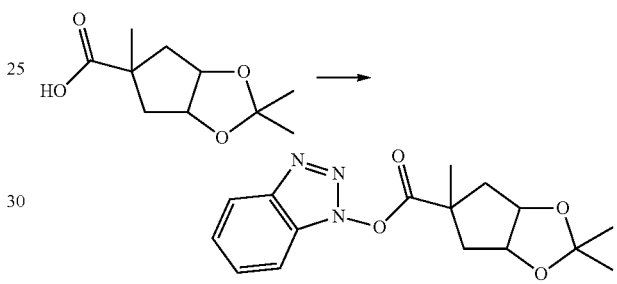

To a solution of 2,2,5-trimethyltetrahydro-3aH-cyclopenta[d][1,3]dioxole-5-carboxylic acid mixed isomers (0.5936 g, 2.964 mmol) in DCM/ACN and excess of TEA was added HBTU (1.239 g, 3.261 mmol, 1.1 eq). Reaction was monitored with TLC for complete disappearance of starting material. DCM/ACN was distilled off under vacuum and the mixture was purified with silica Hex:EtOAc (4:1) to afford two separate diasteriomers as white solid (2.371 mmol, MW 317.34 g/mol, 80%, combined isomers). $^1H$ NMR (700 MHz, $CDCl_3$): Isomer I: δ 1.366(s, 3H), 1.595; (s, 3H), 1.864; (s 3H), 2.28-2.30; (d, 2H, J=14.72 Hz), 2.51-2.53; (dd, 2H), 4.87-4.88; (d, 2H), 7.37-7.38; (d, 1H, J=8.28 Hz), 7.44-4.46; (dd, 1H), 7.56-7.58; (t, 1H, J=7.58 Hz), 8.09-8.10; (d, 1H, J=8.43 Hz); $^1H$ NMR (700 MHz, $CDCl_3$) Isomer II: δ 1.273(s,3H), 1.344; (s, 3H), 1.54-1.57; (dd, 2H), 1.730; (s 3H), 1.74-1.77; (ddd, 2H, J=15.00, 4.06, 1.37 Hz), 2.95-2.97; (d, 2H, J=15.02 Hz), 4.79-4.81; (d, 2H), 7.37-7.38; (d, 1H, J=8.28 Hz), 7.44-4.46; (dd, 1H), 7.56-7.58; (t, 1H, J=7.58 Hz), 8.09-8.10; (d, 1H, J=8.43 Hz).

(e) 2,2,5-trimethyl-N-propyltetrahydro-3aH-cyclopenta[d][1,3]dioxole-5-carboxamide

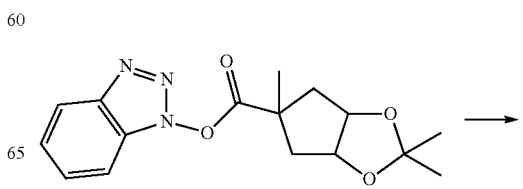

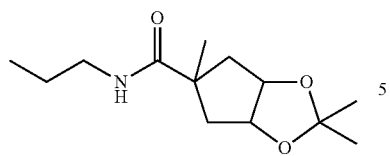

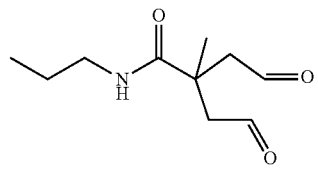

To a solution of 1H-benzo[d][1,2,3]triazol-1-yl-2,2,5-trimethyltetrahydro-3aH-cyclopenta[d][1,3]dioxole-5-carboxylate, Isomer II (0.3769 g, 1.1876 mmol) in dry DCM was added large excess of propyl amine. Mixture was stirred for 0.5 h, then concentrated and flushed through a pad of silica to afford white solid (1.1876 mmol, MW 226.29 g/mol, 100%). $^1$H NMR (400 MHz, CDCl$_3$): δ 0.91-0.95; (t, 3H, J=7.44 Hz), 1.32; (s, 3H), 1.49; (s, 3H), 1.537; (s, 3H), 1.55-1.57; (d, 2H, J=8.75 Hz), 1.84-1.87; (d, 2H, J=14.19 Hz), 2.25-2.30; (dd, 2H), 3.32-3.25; (q,2H), 4.77-4.78; (dt, 2H, J=3.68, 2.09 Hz), 5.58; (1H, br amide).

(f) 3,4-dihydroxy-1-methyl-N-propylcyclopentanecarboxamide

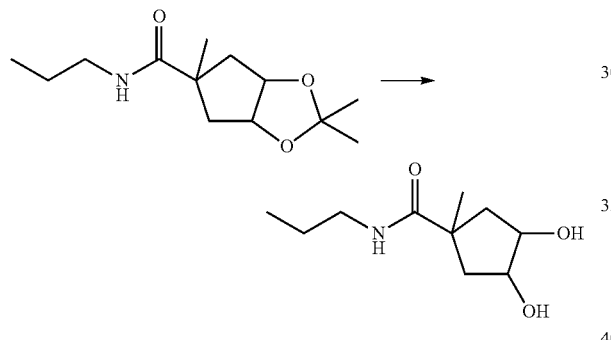

To a solution of 2,2,5-trimethyl-N-propyltetrahydro-3aH-cyclopenta[d][1,3]dioxole-5-carboxamide (0.2687 g, 1.1876 mmol) in methanol 50 ml, 3 drops of 1N HCl was added. Reaction was monitored with TLC for complete disappearance of starting material. Solvent was distilled off under vacuum and the product was taken into ethyl acetate and dried over MgSO$_4$, further purified with silica MeOH:EtOAc (0.5:9.5) to afford a white solid (Mass not obtained, MW 201.26 g/mol) $^1$H NMR (400 MHz, CDCl$_3$): δ 0.905-0.960; (t, 3H, J=7.29 Hz), 1.55; (m,2 H), 1.63-1.68; (dd, 2H, J=13.70, 5.36 Hz), 2.41-2.46; (dd,2H), 3.19-3.24; (q, 2H), 4.24-4.27; (dt, 2H, J=4.70, 2.28 Hz), 5.59; (1H, br amide).

(g) 2-methyl-4-oxa-2-(2-oxoethyl)-N-propylbutanamide

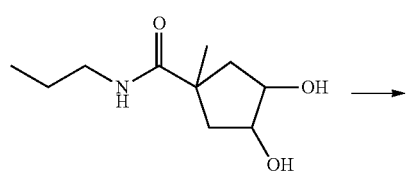

To a solution of 3,4-dihydroxy-1-methyl-N-propylcyclopentanecarboxamide in H$_2$O:methanol (1:9) was added NaIO$_4$. Mixture was stirred for 1 h until a flakey while, solid iodate salt, was obtained. Solvent was distilled off under vacuum and the product was taken into diethyl ether and dried over MgSO$_4$ and used for subsequent reactions. The clear oil could not be purified using any conventional chromatographic systems. $^1$H NMR: molecule was not purified as isolated product.

Example 7

Preparation of Small Molecule-Containing Compound of Formula I

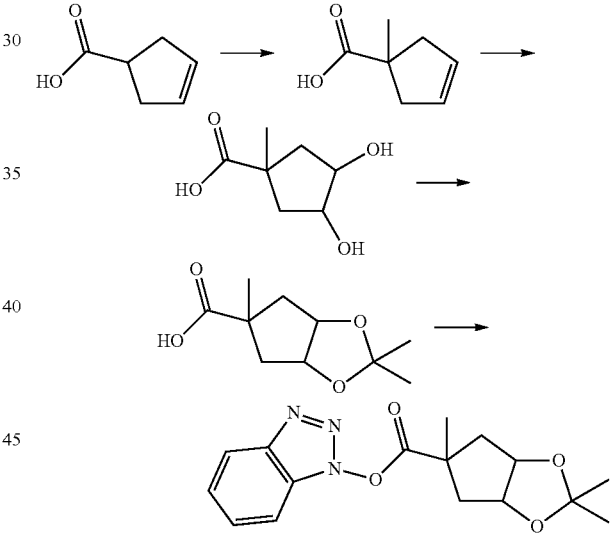

Conversion of 1-methylcyclopent-3-enecarboxylic acid to 1H-benzo[d][1,2,3]triazol-1-yl-2,2,5-trimethyltetrahydro-3a-H-cyclopenta[d][1,3]dioxole-5-carboxylate as documented above.

(a) 2,2,5-trimethyl-N-phenethyltetrahydro-3aH-cyclopenta[d][1,3]dioxole-5-carboxamide

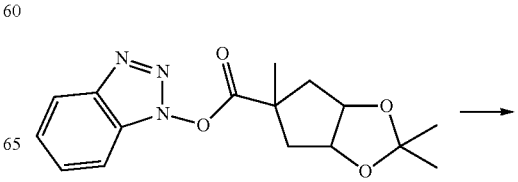

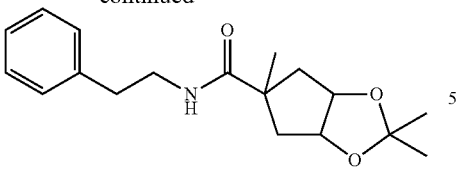

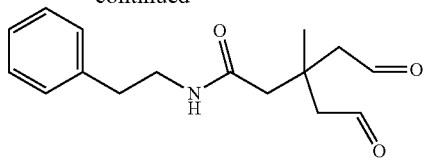

1H-benzo[d][1,2,3]triazol-1-yl-2,2,5-trimethyltetrahydro-3a-H-cyclopenta[d][1,3]dioxole-5-carboxylate in dry DCM was added large excess of phenyl ethyl amine. Mixture was stirred for 0.5 h, then concentrated and flushed through a pad of silica to afford white solid (1.1876 mmol, MW 226.29 g/mol, 100%).1H NMR (400 MHz, CDCl₃): δ 0.91-0.95; (t, 3H, J=7.44 Hz), 1.32; (s, 3H), 1.49; (s, 3H), 1.537; (s, 3H), 1.55-1.57; (d, 2H, J=8.75 Hz), 1.84-1.87; (d, 2H, J=14.19 Hz), 2.25-2.30; (dd, 2H), 3.32-3.25; (q,2H), 4.77-4.78; (dt, 2H, J=3.68, 2.09 Hz), 5.58; (1H, br amide), 7.12-7.64; (m, 5H).

(b) 3,4-dihydroxy-1-methyl-N-phenethylcyclopentanecarboxamide

To a solution of 3,4-dihydroxy-1-methyl-N-phenethylcyclopentanecarboxamide in H₂O:methanol (1:9) was added NaIO₄. Mixture was stirred for 1 h until a flakey white, solid iodate salt, was obtained. Solvent was distilled off under vacuum and the product was taken into diethyl ether and dried over MgSO₄ and used for subsequent reactions. The clear oil could not be purified using any conventional chromatographic systems. ¹H NMR: molecule was not purified as isolated product.

Example 8

Preparation of Lipid-Containing Compound of Formula I (a) cyclopent-3-enylmethanol

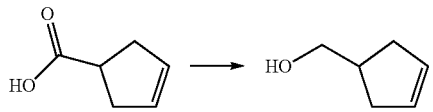 [SMILES: O=C(O)C1CC=CC1 ; OCC1CC=CC1]

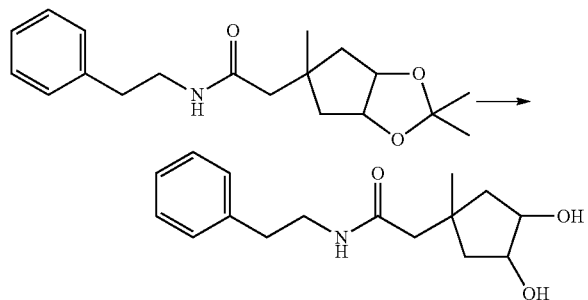

To a solution of 2,2,5-trimethyl-N-phenethyltetrahydro-3aH-cyclopenta[d][1,3]dioxole-5-carboxamide (0.1000 g, 0.3295 mmol) in methanol 50 ml, 3 drops of 1N HCl was added. Reaction was monitored with TLC for complete disappearance of starting material. Solvent was distilled off under vacuum and the product was taken into ethyl acetate and dried over MgSO₄, further purified with silica MeOH: EtOAc (0.5:9.5) to afford a white solid as mixture of isomers (0.3131 mmol, MW 263.33 g/mol, 95%). ¹H NMR (400 MHz, CDCl₃): δ 1.21; (s, 3H), 1.33; (s, 3H), 1.58-1.3; (dd, 2H, J=13.60, 5.16 Hz), 1.72-1.77; (dd, 2H, J=14.12, 6.01 Hz), 2.05-2.10; (dd, 2H, J=14.28, 4.35), 2.32-2.37; (dd, 2H, J=13.64, 6.30 Hz), 2.81-2.86; (q, 2H), 3.48-3.56; (dq, 2H, J=11.70, 6.03 Hz), 4.08-4.1; (dt, 2H, J=4.05 Hz), 4.18-4.22; (dt, 2H, J=4.35 Hz), 5.59; (1H, br amide), 6.17; (1H, br amide), 7.18-7.35; (m, 5H).

(c) 2-methyl-4-oxo-2-(2-oxoethyl)-N-phenethylbutanamide

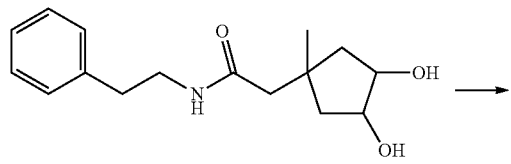

To a suspension of lithium aluminum hydride (0.5083 g, 13.37 mmol, 3 eq) in dry 100 ml THF at −78° C., cyclopent-3-enecarboxylic acid (0.5000 g, 4.45 mmol) was added drop wise over 1 h. The mixture was stirred for 6 h, and then quenched with 15 ml 1M NaOH. Mixture was stirred for an additional 2 h, then concentrated and up taken in diethyl ether and dried over MgSO₄ to afford clear liquid (3.79 mmol, MW 98.14 g/mol, 85%). ¹H NMR (300 MHz, CDCl₃): δ 2.12-2.16; (ttt 1H), 2.49-2.53; (dd, 2H), 3.57-3.58; (d, 3H, 5.14 Hz), 5.69; (s, 2H).

(b) 4-(dodecyloxymethyl)cyclopent-1-ene

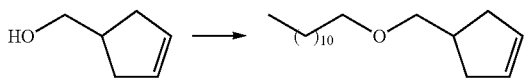

To a suspension of excess NaH in dry 100 ml dry THF al −78° C. was added compound cyclopent-3-enylmethanol (0.3720 g, 3.79 mmol) and stirred for 1 h. Temperature was gradually increased to −40° C. and bromododecane (1.3828 g, 5.68 mmol, 1.5 eq) was added drop wise over 0.5 h. The mixture was mildly refluxed overnight. THF was distilled off under vacuum and the mixture was diluted with DCM. The organic solution was filtered and washed with H₂O (6×50 mL), saturated NH₄Cl (3×50 mL), and H₂O (2×50 mL), dried over MgSO₄, and purified with silica Hex:EtOAc (2:8) to afford a clear oil solid (2.95 mmol, MW 266.46 g/mol, 78%). ¹H NMR (700 MHz, CDCl₃): δ 0.89-0.91; (t, 3H, J=7.04), 1.29-1.35; (m), 1.56-1.59; (dd, 2H, J=13.35, 6.06 Hz), 2.09-2.12; (dd, 2H, J=14.07, 4.72 Hz), 2.47-2.5; (dd, 2H, J=14.14, 8.75 Hz), 2.57-2.60; (tt, 1H, J=8.39,4.13 Hz), 3.32-3.33; (d, 2H, J=7.41 Hz), 3.42-3.44; (t, 2H, J=6.72 Hz), 5.63; (s, 1H).

(c) 4-(dodecyloxymethyl)cyclopentane-1,2-diol

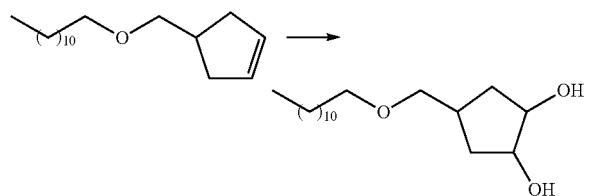

To a solution of 4-(dodecyloxymethyl)cyclopent-1-ene (3.541 g, 2.95 mmol) in acetone: acetonilrile (1:1) was added catalytic amount of OsO$_4$ and excess N-Methylmorpholine N-oxide 50% in H$_2$O. Reaction was monitored with TLC for complete disappearance of starting material. Solvent was distilled off under vacuum and the product was taken into diethyl ether and dried over MgSO$_4$, further purified with silica Hex:EtOAc (3:7) to afford a white solid (2.065 mmol, MW 266.46 g/mol, 70%). $^1$HNMR (400 MHz, CDCl$_3$): δ 0.89-0.91; (t,2H, 7.09 Hz), 1.30-1.33; (m, H), 1.65-1.69; (dt, 2H, 13.88, 6.65 Hz), 0.85-1.89; (m, 2H), 2.56-2.59; (m, 1H), 3.39-3.44; (dt, 4H, J=17.41, 6.71 Hz), 4.151-4.154; (t, 2H, 0.85 Hz).

(d) 3-(dodecyloxymethyl)pentanedial

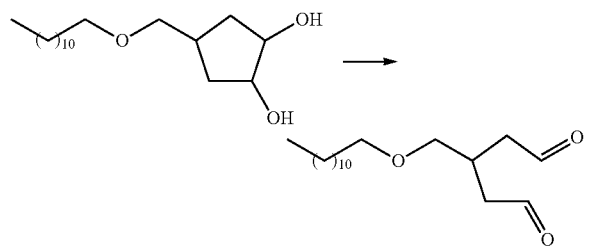

To a solution of 4-(dodecyloxymethyl)cyclopentane-1,2-diol in H$_2$O:methanol (1:9) was added NaIO$_4$. Mixture was stirred for 1 h until a flakey white, solid iodate salt, was obtained. Solvent was distilled off under vacuum and the product was taken into diethyl ether and dried over MgSO$_4$ and used for subsequent reactions. The clear oil could not be purified using any conventional chromatographic systems. $^1$H NMR: molecule was not purified as isolated product.

Example 9

Preparation of Lipid-Containing Compound of Formula I (a) (1-methylcyclopent-3-enyl)methanol

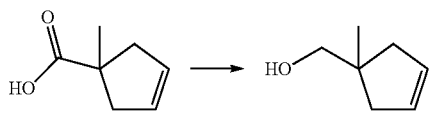

To a suspension of lithium aluminum hydride (0.3358 g, 8.837 mmol, 3 eq) in dry 100 ml THF at −78° C., cyclopent-3-enecarboxylic acid (0.3716 g, 2.945 mmol) was added drop wise over 1 h. The mixture was stirred for 6 h, and then quenched with 15 ml 1M NaOH. Mixture was stirred for an additional 2 h, then concentrated and up taken in diethyl ether and dried over MgSO$_4$ to afford clear liquid (1.885 mmol, MW 112.17 g/mol, 63%). $^1$H NMR (300 MHz, CDCl$_3$): δ 1.13; (s, 3H), 2.07-2.10; (m, 2H), 2.32-2.35; (m, 2H), 3.47; (s, 2H), 5.63; (s, 2H).

(b) 4-(dodecyloxymethyl)-4-methylcyclopent-1-ene

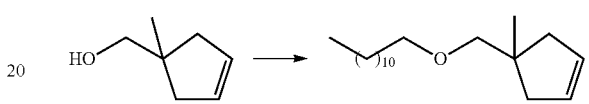

To a suspension of excess NaH in dry 100 ml dry THF at −78° C. was added (1-methylcyclopent-3-enyl)methanol (0.2081 g, 1.885 mmol) and stirred for 1 h. Temperature was gradually increased to −40° C. and bromododecane (0.6107 g, 2.450 mmol, 1.3 eq) was added drop wise over 0.5 h. The mixture was mildly refluxed overnight. THF was distilled off under vacuum and the mixture was diluted with DCM. The organic solution was filtered and washed with H$_2$O (6×50 mL), saturated NH$_4$Cl (3×50 mL), and H$_2$O (2×50 mL), dried over MgSO$_4$. Separation of bromododecane and the ether endured great difficulties; hence the molecule was never purified as isolated product and was directly used in the subsequent reaction.

(c) 4-(dodecyloxymethyl)-4-methylcyclopenlane-1,2-diol

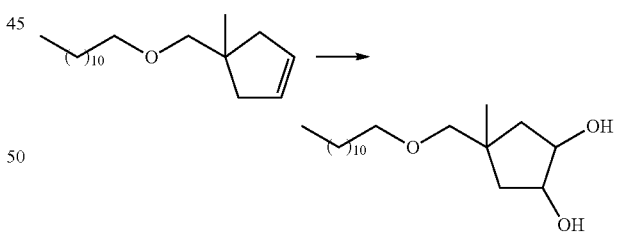

To a solution of crude 4-(dodecyloxymethyl)-4-methyl-cyclopent-1-ene (0.5000 g) in acetone: acetonitrile (1:1) was added catalytic amount of OsO$_4$ and excess N-Methylmorpholine N-oxide 50% in H$_2$O. Reaction was monitored with TLC for complete disappearance of starting material. Solvent was distilled off under vacuum and the product was taken into ethyl acetate and dried over MgSO$_4$, further purified with silica Hex:EtOAc (2.5:2.5) to afford a white solid as mixture of isomers (MW 314.50 g/mol, immeasurable). $^1$H NMR (700 MHz, CDCl$_3$): δ 0.89-0.91; (t, 3H), 1.02; (s, 3H), 1.15; (s, 3H), 1.28; (m, H), 1.61-1.64; (m, 2H), 1.67-1.71; (dd, 2H, J-14.11, 6.41 Hz), 1.78-1.80; (dd, 2H), 1.95-1.97; (dd, 2H, 13.62, 6.51 Hz), 3.06; (s, 2H), 3.13; (s, 2H), 3.38-3.40; (t, 2H, J=6.55 Hz), 3.51-3.53; (t, 2H, J=6.68 Hz), 3.39-3.98; (m, 2H), 4.13-4.16; (m,2H).

(d) 3-(dodecyloxymethyl)-3-methylpentanedial

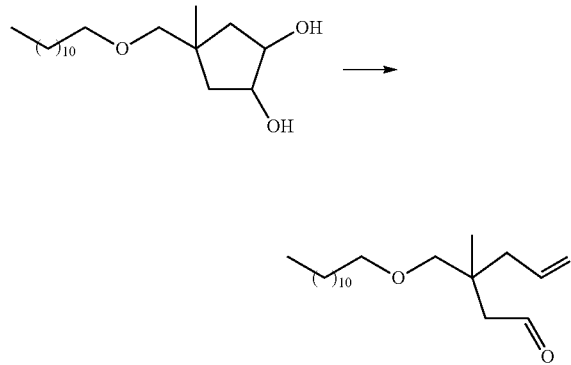

To a solution of 4-(dodecyloxymethyl)-4-methylcyclopentane-1,2-diol in H$_2$O:methanol (1:9) was added NaIO$_4$. Mixture was stirred for 1 h until a flakey white, solid iodate salt, was obtained. Solvent was distilled off under vacuum and the product was taken into diethyl ether and dried over MgSO$_4$ and used for subsequent reactions. The clear oil could not be purified using any conventional chromatographic systems. $^1$H NMR: molecule was not purified as isolated product.

Example 10

Preparation of Biotin-Containing Compound of Formula I (a) 2,2,5-trimethyl-N-(3-(5-((3aS,4S,6aR)-2-oxo-hexahydro-1H-thieno[3,4-d]imidazol-4-yl)pentanamido)propyl)tetrahydro-3aH-cyclopenta[d][1,3]dioxole-5-carboxamide

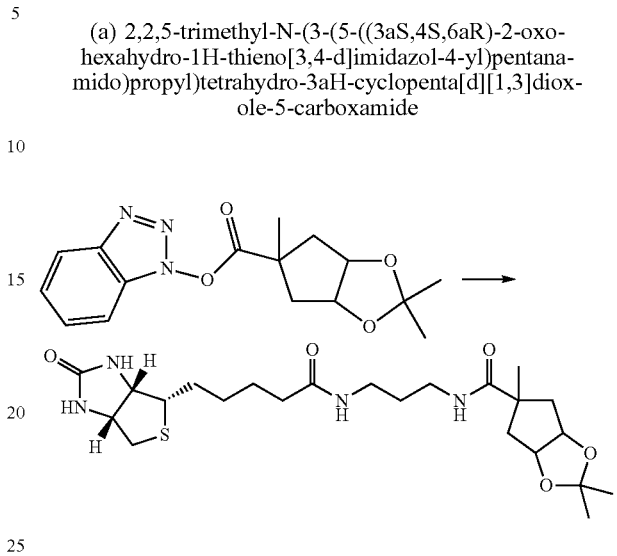

To a solution of 1H-benzo[d][1,2,3]triazol-1-yl-2,2,5-trimethyltetrahydro-3aH-cyclopenta[d][1,3]dioxole-5-carboxylate Isomer II (42.0 mg, 0.1327 mmol) in methanol, N-(+)-Biotinyl-3-aminopropylammonium trifluoroacetate (50 mg, 0.1206 mmol) was added. Mixture was stirred for 10 min in presence of excess sodium bicarbonate, then concentrated and purified with silica EtOAc:MeOH (4.5:0.5) to afford white solid (0.1194 mmol, 90%). [HRMS]m/z: [M+Na]$^+$ Calcd for C$_{23}$H$_{38}$N$_4$O$_5$S is 482.26: found 482.22.

(b) 3,4-dihydroxy-1-methyl-N-(3-(5-((3aS,4S,6aR)-2-oxohexahydro-1H-thieno[3,4-d]imidazol-4-yl)pentanamido)propyl)cyclopentanecarboxamide

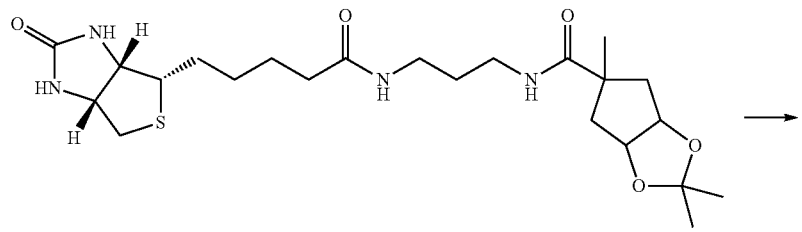

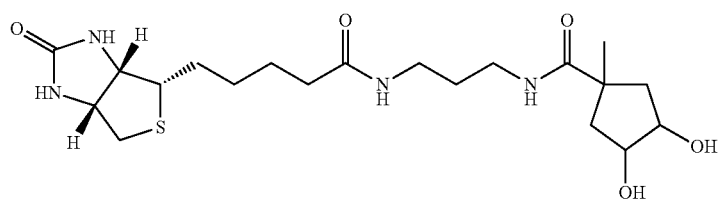

To a solution of (a) (57.64 mg, 0.1194 mmol) in methanol 50 ml, 3 drops of 1N HCl was added. Reaction was monitored with TLC for complete disappearance of starting material. Solvent was distilled off under vacuum and the product was taken into methanol and neutralized with sodium bicarbonate and dried over MgSO$_4$, further purified with silica MeOH:EtOAc (0.5:9.5) to afford a white solid (0.1134 mmol, 95%). [HRMS] m/z: [M+Na]$^+$ Calcd for $C_{20}H_{34}N_4O_5S$ is 442.22: found 442.30.

(c) N-(3-(2-methyl-4-oxo-2-(2-oxoethyl)butanamido)propyl)-5-((3aS,4S,6aR)-2-oxohexahydro-1H-thieno[3,4-d]imidazol-4-yl)pentanamide

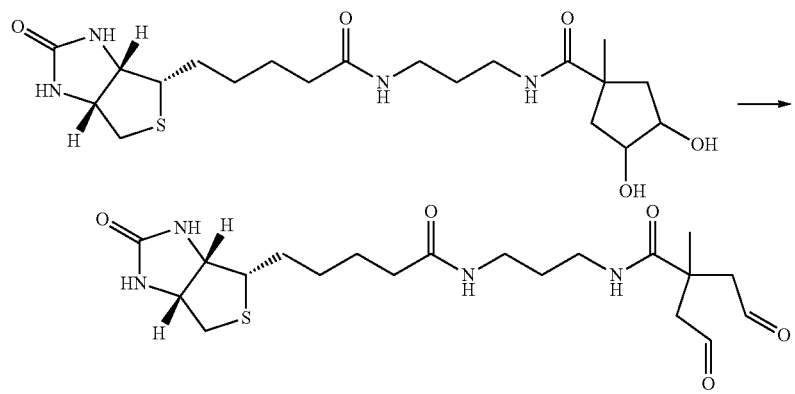

To a solution of (b) in H$_2$O:methanol (1:9) was added NaIO$_4$. Mixture was stirred for 1 h until a flakey white, solid iodate salt, was obtained. Solvent was distilled off under vacuum and the product was taken into methanol and dried over MgSO$_4$ and used for subsequent reactions. The clear oil could not be purified using any conventional chromatographic systems. $^1$H NMR: molecule was not purified as isolated product.

Example 11

Preparation of 2,4-dinitrophenyl-Containing Compound of Formula I (a) N-(8-(2,4-dinitrophenylamino)octyl)-1-methylcyclopent-3-enecarboxamide

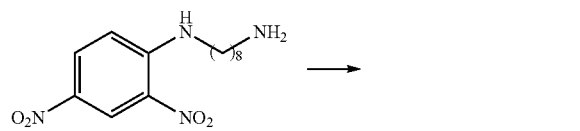

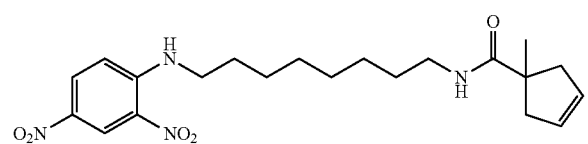

To a solution of N1-(2,4-dinitrophenyl)octane-1,8-diamine (0.5000 g, 1.2376 mmol) in MeOH was added (0.2845 g, 1.361 mmol, 1.1eq) of 2-(((1-methylcyclopent-3-enecarbonyl)oxy)amino)cyclopentane-1,3-dione. Mixture was stirred for 1 h, then concentrated and flushed through a pad of silica to afford yellow solid (1.076 mmol, MW 404.46 g/mol, 87%). $^1$H NMR (700 MHz, MeOD): δ 1.35-1.48; (m, 4H), 1.47-1.54; (m, 4H), 1.75-1.79; (dt, 4H,J=14.68, 7.39 Hz), 2.52-2.61; (m, 4H), 2.99-3.03; (tt, 1H, J=9.21, 7.66 Hz), 3.17-3.19; (t, 2H, J=7.12 Hz), 3.49-3.51; (t, 2H, J=7.20 Hz), 5.66; (s, 2H), 7.17-7.18; (d, 1H, J=9.58 Hz), 8.30-8.31; (m, 2H), 9.05-9.06; (t, 1H, J=2.32 Hz).

(b) N-(8-(2,4-dinitrophenylamino)octyl)-3,4-dihydroxy-1-methylcyclopenlanecarboxamide

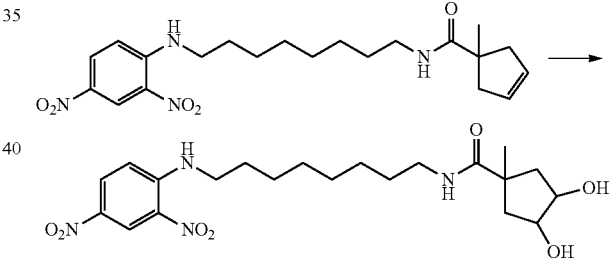

To a solution of (a) (0.4347 g, 1.076 mmol) in acetone:acetonitrile (1:1) was added catalytic amount of OsO$_4$ and excess N-methylmorpholine N-oxide 50% in H$_2$O. Reaction was monitored with TLC for complete disappearance of starting material. Solvent was distilled off under vacuum and the product was taken into ethylacetate and dried over MgSO$_4$, further purified with silica Hex:EtOAc (3:7) to afford two separate diasteriomers as yellow solid (0.7854 mmol, MW 438.47 g/mol, 73%). $^1$H NMR (700 MHz, CDCl$_3$): Isomer I: δ 1.35-1.45; (m, 2H), 1.46-1.53; (tt, 2H, J=15.46, 7.70 Hz), 1.75-1.79; (dt, 2H), 1.86-1.90; (m, 2H), 1.92-1.96; (m, 2H), 2.97-3.02; (tt,1H, J=9.49, 6.75 Hz), 3.14-3.16; (t, 2H, J=7.11 Hz), 3.49-3.51; (t, 2H, J= 7.20 Hz), 4.10-4.12; (m, 2H), 7.17-7.18; (d, 1H, J=9.58 Hz), 8.30-8.31; (m, 2H), 9.05-9.06; (t, 1H, J=2.32 Hz). $^1$H NMR (700 MHz, CDCl$_3$): Isomer II: δ 1.34-1.46; (m, 2H), 1.46-1.54; (ddt, 2H, J=22.49, 15.00, 7.43 Hz), 1.75-1.82; (m, 2H), 2.11-2.15; (m, 2H), 2.70-2.75; (tt, 2H, J=9.28, 6.45 Hz), 3.16-3.18; (t, 2H, J=7.08 Hz), 3.49-3.51; (t, 2H, J=7.19 Hz), 3.93-3.96; (m, 1H), 7.17-7.18; (d, 1H, J=9.58 Hz), 8.30-8.31; (m, 2H), 9.05-9.06; (t, 1H, J=2.32 Hz).

(c) N-(8-(2,4-dinitrophenylamino)octyl)-4-oxo-2-(2-oxoethyl)butanamide

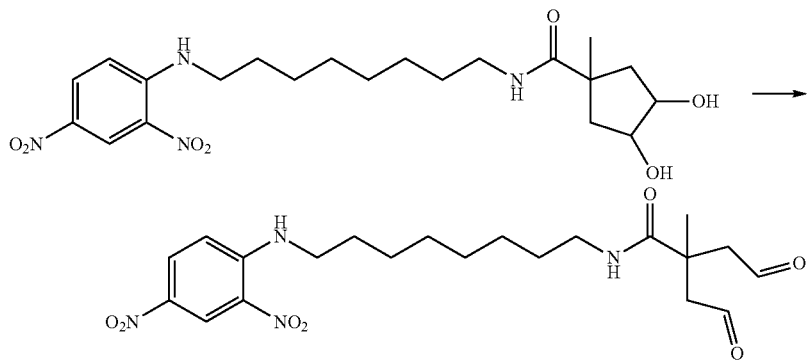

To a solution of (b) in H₂O:methanol (1:9) was added NaIO₄. Mixture was stirred for 1 h until a flakey white, solid iodate salt, was obtained. Solvent was distilled off under vacuum and the product was taken into methanol and dried over MgSO₄ and used for subsequent reactions. The clear oil could not be purified using any conventional chromatographic systems. ¹H NMR: molecule was not purified as isolated product.

Example 12

Preparation of 2,4-dinitrophenyl and Biotin-Containing Compound of Formula I with a CH₂(O)(CH2)C(O)O Linker

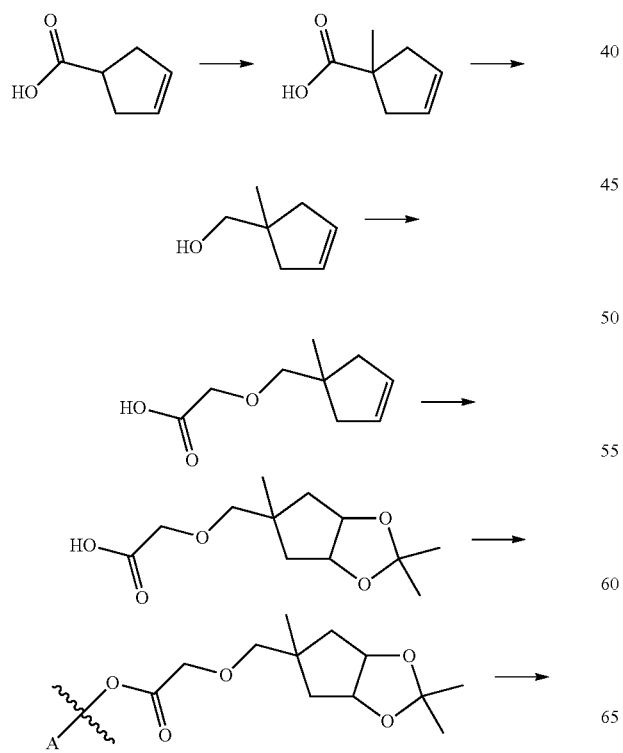

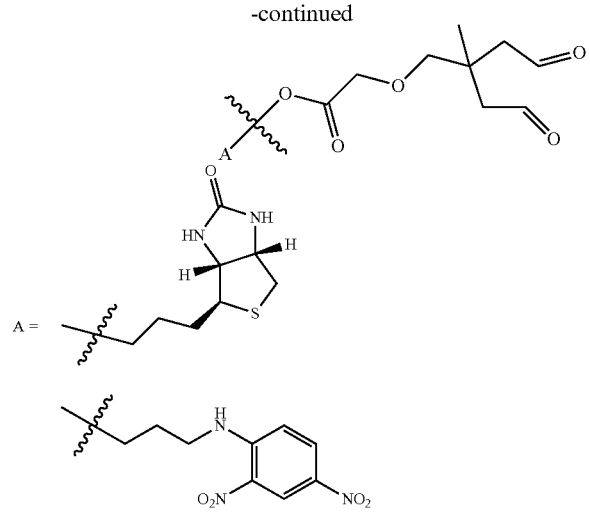

(a) 2-((1-methylcyclopent-3-enyl)methoxy)acetic acid

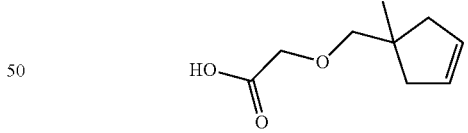

To a suspension of excess NaH in dry 100 ml dry THF at −78° C. was added (1-methylcyclopent-3-enyl)methanol (0.2642 g, 2.356 mmol) and stirred for 1 h. Temperature was gradually increased to −40° C. and 2-chloroacetic acid (0.3358 g, 3.5340 mmol) was added drop wise over 0.5 h. The mixture was mildly refluxed overnight. THF was distilled off under vacuum and the mixture was diluted with DCM. The organic solution was filtered and washed with H₂O (6×50 mL), saturated NH₄Cl (3×50 mL), and H₂O (2×50 mL), dried over MgSO₄, and purified with silica Hex:EtOAc (2:8) to afford a clear oil solid.

(b) 2-((3,4-dihydroxy-1-methylcyclopentyl)methoxy)acetic acid

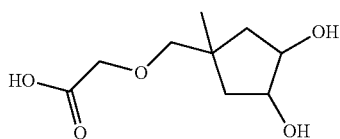

To a solution of (a) (0.3400 g, 2.002 mmol) in acetone:acetonitrile (1:1) was added catalytic amount of OsO$_4$ and excess N-Methylmorpholine N-oxide 50% in H$_2$O. Reaction was monitored with TLC for complete disappearance of starting material. Solvent was distilled off under vacuum and the product was taken into ethyl acetate and dried over MgSO$_4$, further purified with silica gel MeOH:LtOAc (0.5:9.5) to afford a clear oil.

(c) 2-((2,2,5-trimethyltetrahydro-3a-H-cyclopenta[d][1,3]dioxol-5-yl)methoxy)acetic acid

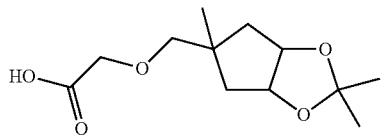 [SMILES: CC1(COCC(=O)O)CC2OC(C)(C)OC2C1]

To a solution of (b) (0.3400 g, 2.002 mmol) in dry THF and catalytic amount of p-TsOH was added large excess of 2,2-dimethoxypropane. Reaction was monitored with TLC for complete disappearance of starting material. THF was distilled off under vacuum and the mixture was diluted with DCM. The organic solution was filtered and washed with H$_2$O (2×50 mL), dried over MgSO$_4$, and purified with silica Hex:EtOAc (7:3) to afford mixture of diasteriomers as white solid.

(d) 1H-benzo[d][1,2,3]triazol-1-yl-2,2,5-trimethyl-tetrahydro-3aH-cyclopenta[d][1,3]dioxole-5-carboxylate probe

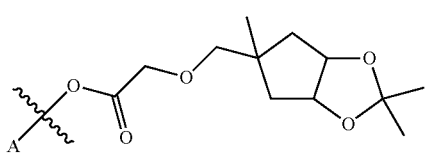

To a solution of (c) mixed isomers (0.3400 g, 2.002 mmol) in DCM/ACN and excess of TEA was added HBTU (1.1414 g, 3.003 mmol, 1.5eq). Reaction was monitored with TLC for complete disappearance of starting material. After 1 h the probe displaying amine functional group was introduced at 1 mole ratio to carboxylic acid in suitable solvent and stirred for another 15 min. The solvent was distilled off under vacuum and the mixture was purified with silica gel to afford the product.

(1) 5-((3aS, 4S, 6aR)-3a, 6a-dimethyl-2-oxohexahydro-1H-thieno[3,4-d]imidazol-4-yl)-N-(3-(2-((2,2,5-trimeihyltetrahydro-3aH-cyclopenta[d][1,3]dioxol-5-yl)methoxy)acetamido)propyl)penlanamide

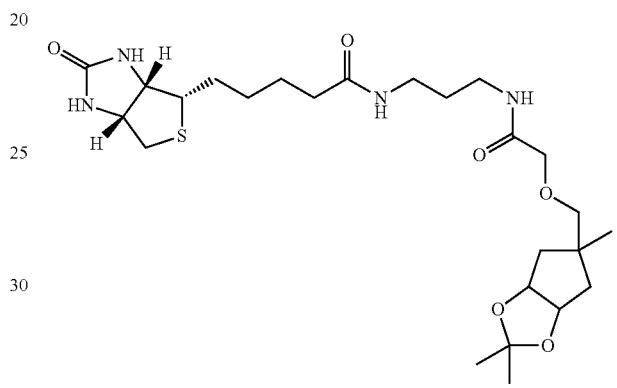

To a solution of (c) mixed isomers (0.0882 g, 0.3618 mmol) in DCM/ACN and excess of TEA was added HBTU (0.1649, 0.4341 mmol, 1.2eq). Reaction was monitored with TLC for complete disappearance of starting material. After 1 h N-(+)-Biotinyl-3-aminopropylammonium trifluoroacetate (100 mg, 0.2412 mmol) is introduced in methanol and stirred for another 15 min. The solvent was distilled off under vacuum and the mixture was purified with silica gel to afford the product.

(2) N-(6-(2,4-dinitrophenylamino)hexyl)-2-((2,2,5-trimethyltetrahydro-3aH-cyclopenta[d][1,3]dioxol-5-yl)methoxy)acetamide

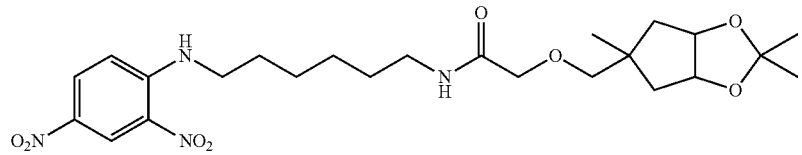 [SMILES: CC1(COCC(=O)NCCCCCCNc2ccc([N+](=O)[O-])cc2[N+](=O)[O-])CC2OC(C)(C)OC2C1]

To a solution of (c) mixed isomers (0.0882 g, 0.3618 mmol) in DCM/ACN and excess of TEA was added HBTU (0.1649, 0.4341 mmol, 1.2eq). Reaction was monitored with TLC for complete disappearance of starting material. After 1 h DNA cadaverine (68 mg, 0.2412 mmol) is introduced in DCM and stirred for another 15 min. The solvent was distilled off under vacuum and the mixture was purified with silica gel to afford the product.

(e) 5-((3aS,4S,6aR)-3a,6a-Dimethyl-2-Oxohexahydro-1H-thieno[3,4-d]imidazol-4-yl)-N-(3-(2-(2-methyl-4-oxo-2-(2-oxoethyl)butoxy)acetamido)propyl)pentanamide

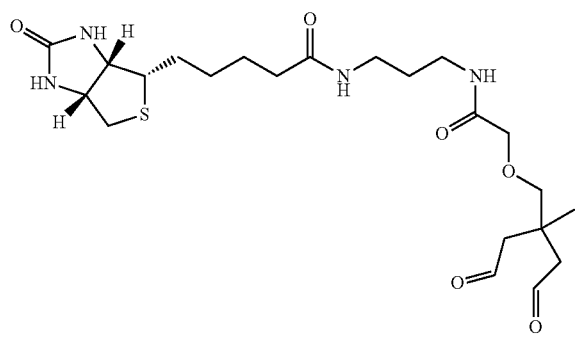 [SMILES: CC(CC=O)(CC=O)COCC(=O)NCCCNC(=O)CCCC[C@@H]1SC[C@@H]2NC(=O)N[C@@H]21]

To a solution of (d1) in H$_2$O:methanol (1:9) was added NaIO$_4$. Mixture was stirred for 1 h until a flakey white, solid iodate salt, was obtained. Solvent was distilled off under vacuum and the product was taken into diethyl ether and dried over MgSO$_4$ and used for subsequent reactions.

(f) N-(6-(2,4-dinitrophenylamino)hexyl)-2-(2-methyl-4-oxo-2-(2-oxoethyl)butoxy)acetamide

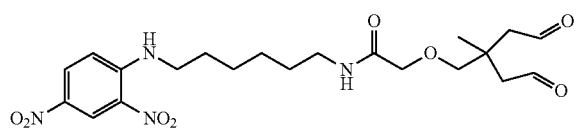 [SMILES: CC(CC=O)(CC=O)COCC(=O)NCCCCCCNc1ccc([N+](=O)[O-])cc1[N+](=O)[O-]]

To a solution of (d2) in H$_2$O:methanol (1:9) was added NaIO$_4$. Mixture was stirred for 1 h until a flakey white, solid iodate salt, was obtained. Solvent was distilled off under vacuum and the product was taken into diethyl ether and dried over MgSO$_4$ and used for subsequent reactions.

Example 13

Generation of Aromatic Dialdehyde (a) Bis (dibromomethyl) benzoic acid

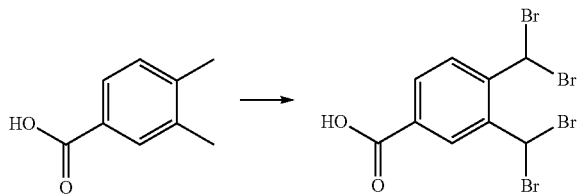

Bis(dibromomethyl)benzoic acid was synthesized from commercially available 3,4-dimethylbenzoic acid. 3,4-Dimethylbenzoic acid (960.0 g, 30.0 mmol) was dissolved in warm carbon tetrachloride (40 mL). N-Bromosuccinimide (28.9 g, 162 mmol) and benzoyl peroxide (0.81 g, 3.35 mmol) were added slowly and the reaction mixture was refluxed overnight. After cooling down, the white precipitate was filtered and washed twice with toluene (60 mL) and diethyl ether (80 mL). The filtrate was concentrated and the residue was recrystallized in acetonitrile to give the desired product as a white solid (9.54 g, 51%). $^1$H NMR (400 MHz, D6-DMSO): δ 13.53; (s, 1H), 8.34; (s, 1H), 7.99; (d, J=7.8 Hz, 1 H), 7.95; (s, 1H), 7.78; (s, 1H), 7.77; (d, J=7.8 Hz, 1 H).

(b) 1,3-Dimethoxy-1,3-dihydroisobenzofuran-5-carboxylic acid

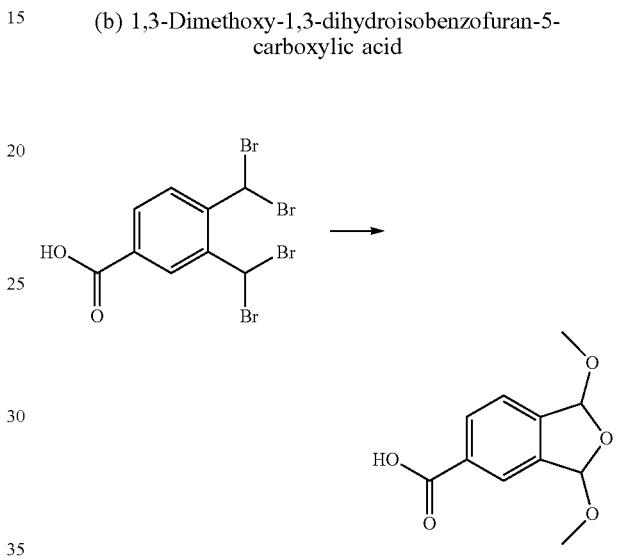

Bis(dibromomethyl) benzoic acid (Example 4(a), 2.0 g, 4.29 mmol) was dissolved in 10% Na$_2$CO$_3$ (20 mL). The reaction mixture was heated at 70° C. for 4 h. After cooling down, the reaction mixture was acidified carefully with concentrated HCl to pH 1, followed by extraction with EtOAc (20 mL) three times. The organic layer was washed with brine (30 ml,), dried with Na$_2$SO$_4$ and concentrated in vacuo. The light yellow solid was then dissolved in dry MeOH (20 mL) and Sc(OTf)$_3$ (100 mg, 0.2 mmol) was added. The reaction mixture was stirred at room temperature overnight. The solvent was then removed in vacuo. The residue was purified by flash chromatography on Si60 in DCM/methanol to afford the target product as a white solid (550 mg, 2.45 mmol, 57%). $^1$H NMR (400 MHz, D6-DMSO): δ 13.21; (br. s, 1H), 8.05;(d, J=7.6 Hz, 1 H), 7.93; (s, 1H), 7.55; (d, J=7.6 Hz, 1 H), 6.36; (s, 1H), 6.11; (s, 1H), 3.37-3.32; (m, 6H).

(c) Aromatic dialdehyde

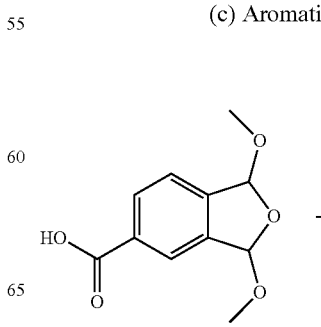

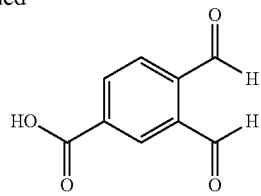

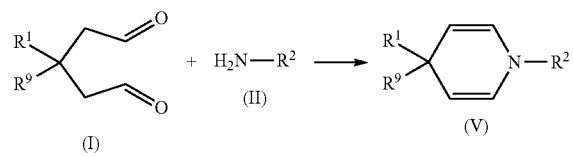

1,3-Dimethoxy-1,3-dihydroisobenzofuran-5-carboxylic acid (Example 4(b), 20 mg, 0.0248 mmol) was treated with TEA (2 mL) and water (2 mL) at room temperature for 2 h. TLC (DCM:methanol=10:1) shown the completion of the reaction. The solvent was removed in vacuo. The residue was purified by preparative RP-HPLC (ACN and 0.1% TFA in water) followed by freeze-drying to afford the product as a white solid (8.0 mg, 0.0105 mmol, 42%).

Example 14

General Conjugation Reaction Conditions between dialdehyde and amine tethered groups The conjugation reaction was performed by reacting 1 equivalent of each of the non-polymeric dialdehyde and primary amine tethered molecules in water (pH 7.0) at room temperature (25° C.) for approximately 20 minutes. Yields were approximately 95% with no purification.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

[1] Nagasaki, Y. et al. U.S. Patent Application Publication No. 2014/0329290, Nov. 6, 2014.
[2] Miao, Z. et al. PCT Patent Application Publication No. 2013/173392, Nov. 21, 2013.
[3] Wagner, Ingrid; Musso, Hans (November 1983). "New Naturally Occurring Amino Acids". *Angew. Chem. Int. Ed. Engl.* 22 (22): 816-828.

The invention claimed is:

1. A method for conjugating a labeling moiety to a compound comprising an $NH_2$ moiety, the method comprising reacting a non-polymeric aliphatic dialdehyde comprising the labeling moiety with the compound comprising the $NH_2$ moiety under conditions for the conjugation of the $NH_2$ moiety with the dialdehyde to form a conjugated product, wherein the non-polymeric aliphatic dialdehyde comprising the labeling moiety is a compound of Formula I and the compound comprising the $NH_2$ moiety is a compound of Formula II, providing a conjugated product of the Formula V:

wherein:
$R^1$ is selected from a fluorescent dye, ligand, radiolabel, spin label, redox molecule, isotope label, and PET label, which is optionally linked to the $C[CH_2C(O)H]_2$ via a linker moiety;
$R^2$ is selected from a ligand, drug, small molecule, protein, antibody, lipid, carbohydrate, nucleic acid, peptide, nanoparticle, polymer, macrocycle, metal complex, solid support and MOF, which is optionally linked to the $NH_2$ via a linker moiety; and
$R^9$ is H or $C_{1-6}$alkyl.

2. The method of claim 1, wherein $R^1$ comprises a linker moiety.

3. The method of claim 2, wherein the linker moiety is selected from $-(CH_2)_p-$, $-(CH_2)_p-S-(CH_2)_{p'}-$, $-(CH_2)_p-O-(CH_2)_{p'}-$, $-(CH_2)_p-C(O)-(CH_2)_{p'}-$, $-(CH_2)_p-C(O)O-(CH_2)_{p'}-$, $-(CH_2)_p-OC(O)(CH_2)_{p'}-$, $-(CH_2)_p-C(O)NH-(CH_2)_{p'}-$, $-(CH_2)_p-NHC(O)-(CH_2)_{p'}-$, $-(CH_2)_p-OC(O)O-(CH_2)_{p'}-$, $-(CH_2)_p-OC(O)NH-(CH_2)_{p'}-$, $-(CH_2)_p-NHC(O)O-(CH_2)_{p'}-$ and $O-(CH_2CH_2O)_p-$ wherein p and p' are independently selected from 0, 1, 2, 3, 4, 5, and 6 and at least one of p and p' is other than 0.

4. The method of claim 1, wherein $R^1$ comprises a molecule selected from biotin, a cyanine dye, fluorescein, rhodamine, ferrocene, boron-dipyrromethene, 2,4-dinitrophenyl (DNP), and nitrobenzodioxazole (NBD).

5. The method of claim 1, wherein $R^2$ is a peptide, a protein, an antibody, a drug, a ligand or a solid support.

6. The method of claim 1, wherein $R^2$ does not comprise a linker moiety.

7. The method of claim 1, wherein $R^9$ is $C_{1-6}$alkyl.

8. The method of claim 1, wherein the compound of Formula I is selected from:

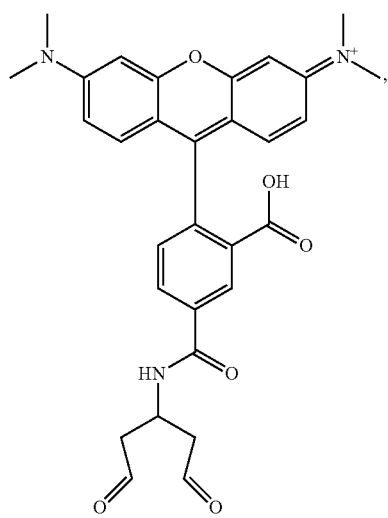

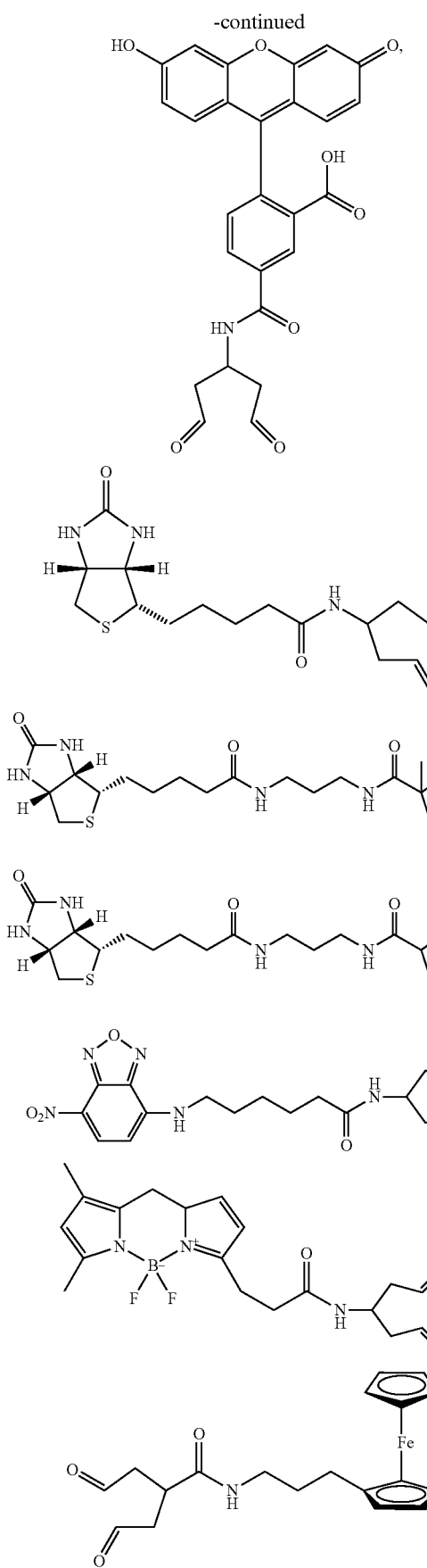

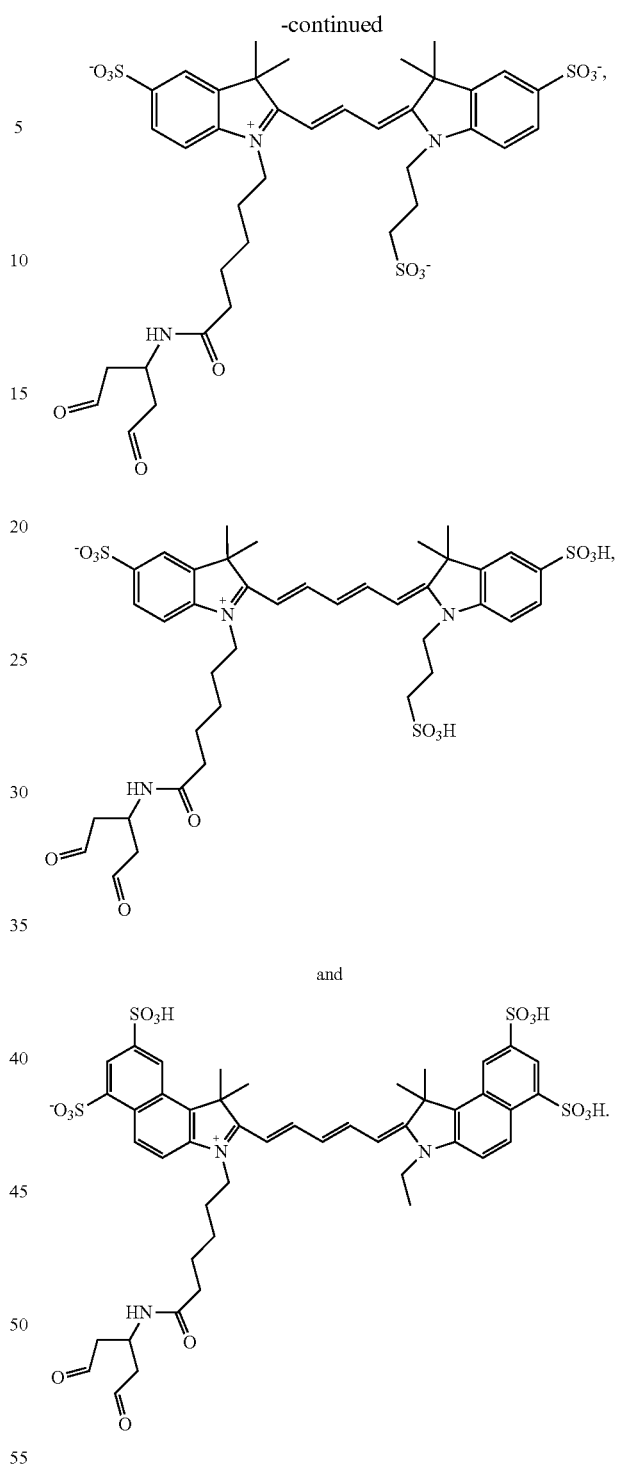

9. A method for conjugating a labeling moiety to a compound comprising an NH₂ moiety, the method comprising reacting a non-polymeric aliphatic dialdehyde comprising the labeling moiety with the compound comprising the NH₂ moiety under conditions for the conjugation of the NH₂ moiety with the dialdehyde to form a conjugated product, wherein the non-polymeric aliphatic dialdehyde comprising the labeling moiety is a compound of Formula I and the compound comprising the NH₂ moiety is a compound of Formula II, providing a conjugated product of the Formula V:

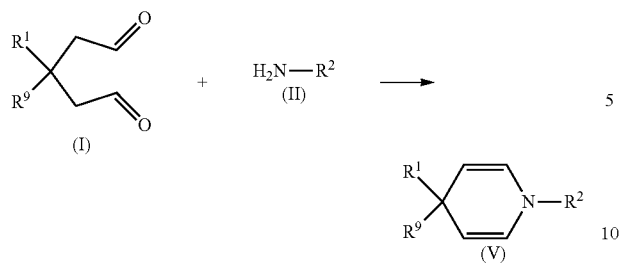

wherein:

R[1] is selected from a fluorescent dye, ligand, radiolabel, spin label, redox molecule, isotope label, and PET label, which is optionally linked to the $C[CH_2C(O)H]_2$ via a linker moiety;

$$H_2N-R^2 \quad (II)$$

R[2] is a biomolecule, which is optionally linked to the $NH_2$ via a linker moiety; and R[9] is H or $C_{1-6}$alkyl, and wherein the conditions for the conjugation of the $NH_2$ moiety with the dialdehyde to form a conjugated product comprise combining aqueous solutions of the non-polymeric aliphatic dialdehyde comprising the labeling moiety and the compound of Formula II.

10. The method of claim 9, wherein the biomolecule is an antibody, protein, peptide or nucleic acid.

11. The method of claim 9, wherein R[9] is $C_{1-6}$alkyl.

12. The method of claim 9, wherein R[1] comprises a linker moiety.

13. The method of claim 12, wherein the linker moiety is selected from $-(CH_2)_p-$, $-(CH_2)_{p'}-S-(CH_2)_p-$, $-(CH_2)_{p'}-O-(CH_2)_p-$, $-(CH_2)_{p'}-C(O)-(CH_2)_p-$, $-(CH_2)_{p'}-C(O)O-(CH_2)_p-$, $-(CH_2)_{p'}-OC(O)(CH_2)_p-$, $-(CH_2)_{p'}-C(O)NH-(CH_2)_p-$, $-(CH_2)_{p'}-NHC(O)-(CH_2)_p-$, $-(CH_2)_{p'}-OC(O)O-(CH_2)_p-$, $-(CH_2)_{p'}-OC(O)NH-(CH_2)_p-$, $-(CH_2)_{p'}-NHC(O)O-(CH_2)_p-$ and $O-(CH_2CH_2O)_p-$ wherein p and p' are independently selected from 0, 1, 2, 3, 4, 5 and 6 and at least one of p and p' is other than 0.

14. The method of claim 11, wherein R[1] comprises a molecule selected from biotin, a cyanine dye, fluorescein, rhodamine, ferrocene, boron-dipyrromethene, 2,4-dinitrophenyl (DNP), and nitrobenzodioxazole (NBD).

15. The method of claim 9, wherein R[2] does not comprise a linker moiety.

16. The method of claim 9, wherein the compound of Formula I is selected from:

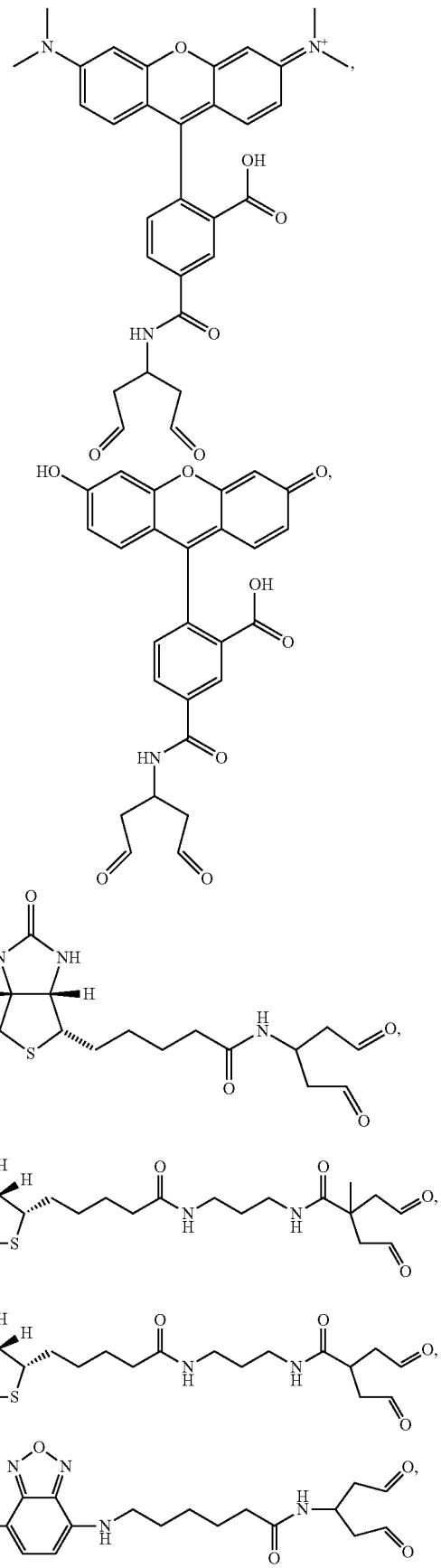

47
-continued
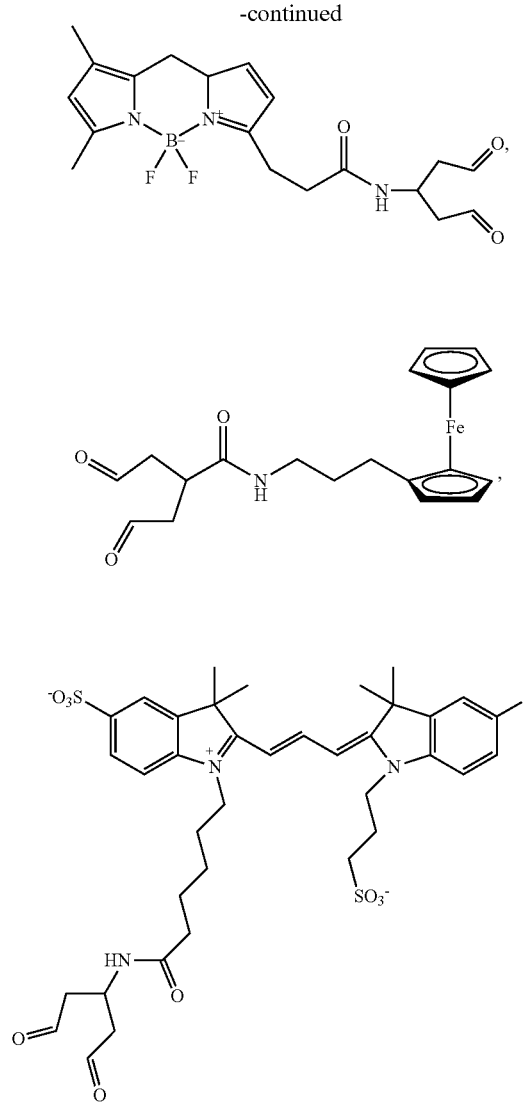
48
-continued
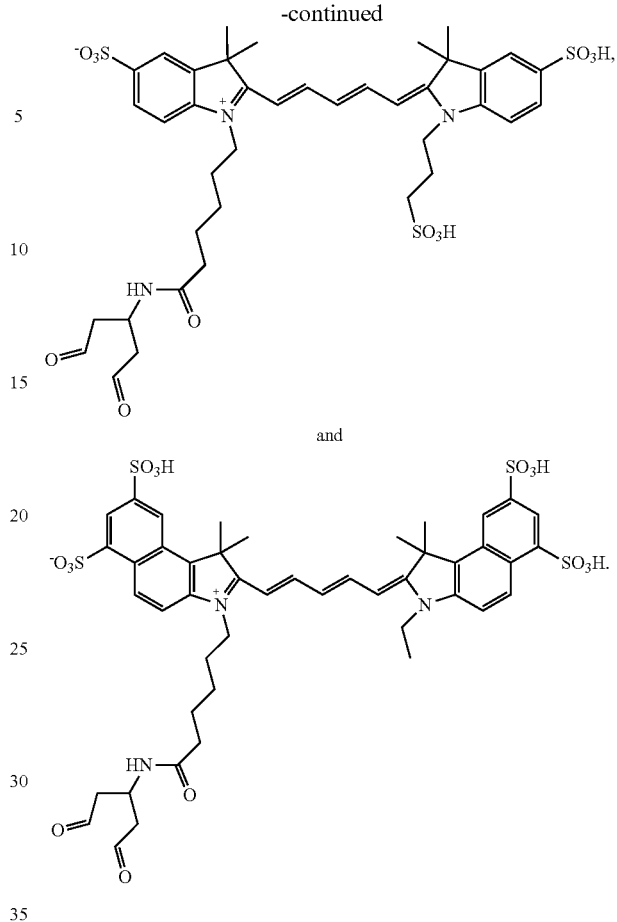
and
17. The method of claim 1, wherein the conditions for the conjugation of the NH$_2$ moiety with the dialdehyde to form a conjugated product comprise combining aqueous solutions of the compound of Formula I and the compound of Formula II.
18. The method of claim 4, wherein R$^9$ is C$_{1-6}$alkyl.
* * * * *